(12) United States Patent
Say

(10) Patent No.: US 9,585,605 B2
(45) Date of Patent: Mar. 7, 2017

(54) FLUID MANAGEMENT AND PATIENT MONITORING SYSTEM

(75) Inventor: James L. Say, Breckenridge, CO (US)

(73) Assignee: Pepex Biomedical, Inc., St. Louis, MO (US)

( * ) Notice: Subject to any disclaimer, the term of this patent is extended or adjusted under 35 U.S.C. 154(b) by 609 days.

(21) Appl. No.: 14/118,687

(22) PCT Filed: May 18, 2012

(86) PCT No.: PCT/US2012/038598
§ 371 (c)(1),
(2), (4) Date: Feb. 19, 2014

(87) PCT Pub. No.: WO2012/159040
PCT Pub. Date: Nov. 22, 2012

(65) Prior Publication Data
US 2014/0163340 A1  Jun. 12, 2014

Related U.S. Application Data

(60) Provisional application No. 61/487,937, filed on May 19, 2011.

(51) Int. Cl.
*A61B 5/05* (2006.01)
*A61B 5/145* (2006.01)
(Continued)

(52) U.S. Cl.
CPC ........ *A61B 5/14546* (2013.01); *A61B 5/1473* (2013.01); *A61B 5/1495* (2013.01); *A61B 5/6866* (2013.01); *A61B 5/14532* (2013.01)

(58) Field of Classification Search
CPC . A61B 5/14546; A61B 5/1473; A61B 5/1495; A61B 5/6866; A61B 5/14532
See application file for complete search history.

(56) References Cited

U.S. PATENT DOCUMENTS 3,766,910 A   10/1973  Lake
3,948,604 A    4/1976  Hoppesch
(Continued)

FOREIGN PATENT DOCUMENTS

EP   0 256 415 A2   2/1988
EP   0 327 658 A1   8/1989
(Continued)

OTHER PUBLICATIONS

International Search Report and Written Opinion from International Application No. PCT/US2012/038598 mailed Nov. 23, 2012.
(Continued)

*Primary Examiner* — Tiffany Weston
(74) *Attorney, Agent, or Firm* — Merchant & Gould P.C.

(57) ABSTRACT

A lactate sensor arrangement includes a catheter for withdrawing a test fluid sample, a sensor module for measuring an analyte such as lactate in the sample, and a pumping mechanism. A single uninterrupted flow path extends between the pumping mechanism and the catheter and within the flow path resides a sensor module containing a test chamber. The sensor arrangement also includes a control unit or controller that interfaces with a pumping mechanism driver. The sensor arrangement also includes a source of sensor calibration and anticoagulant solution, such as a reservoir.

7 Claims, 14 Drawing Sheets

(51) Int. Cl.
*A61B 5/00* (2006.01)
*A61B 5/1473* (2006.01)
*A61B 5/1495* (2006.01)

(56) References Cited

U.S. PATENT DOCUMENTS

| | | | |
|---|---|---|---|
| 4,008,717 A | 2/1977 | Kowarski | |
| 4,221,567 A | 9/1980 | Clark et al. | |
| 4,240,438 A | 12/1980 | Updike et al. | |
| 4,439,303 A | 3/1984 | Cocchi | |
| 4,467,811 A | 8/1984 | Clark | |
| 4,573,968 A | 3/1986 | Parker | |
| 4,640,821 A | 2/1987 | Mody et al. | |
| 4,671,288 A | 6/1987 | Gough | |
| 4,734,184 A | 3/1988 | Burleigh et al. | |
| 4,786,394 A | 11/1988 | Enzer et al. | |
| 4,813,423 A | 3/1989 | Miyasaka et al. | |
| 4,830,011 A | 5/1989 | Lim | |
| 4,833,083 A | 5/1989 | Saxena | |
| 4,841,974 A | 6/1989 | Gumbrecht et al. | |
| 4,908,115 A | 3/1990 | Morita et al. | |
| 4,919,649 A | 4/1990 | Timothy et al. | |
| 4,945,896 A | 8/1990 | Gade | |
| 4,995,867 A | 2/1991 | Zollinger | |
| 5,002,651 A | 3/1991 | Shaw et al. | |
| 5,004,583 A | 4/1991 | Guruswamy et al. | |
| 5,046,496 A | 9/1991 | Betts et al. | |
| 5,097,834 A | 3/1992 | Skrabal | |
| 5,112,455 A | 5/1992 | Cozzette et al. | |
| 5,165,406 A | 11/1992 | Wong | |
| 5,165,407 A | 11/1992 | Wilson et al. | |
| 5,171,689 A | 12/1992 | Kawaguri et al. | |
| 5,220,920 A | 6/1993 | Gharib | |
| 5,234,835 A | 8/1993 | Nestor et al. | |
| 5,243,982 A | 9/1993 | Möstl et al. | |
| 5,262,035 A | 11/1993 | Gregg et al. | |
| 5,264,104 A | 11/1993 | Gregg et al. | |
| 5,264,105 A | 11/1993 | Gregg et al. | |
| 5,271,815 A | 12/1993 | Wong | |
| 5,320,725 A | 6/1994 | Gregg et al. | |
| 5,330,634 A | 7/1994 | Wong et al. | |
| 5,356,786 A | 10/1994 | Heller et al. | |
| D354,347 S | 1/1995 | Knute et al. | |
| D354,559 S | 1/1995 | Knute et al. | |
| 5,384,028 A | 1/1995 | Ito | |
| 5,431,174 A | 7/1995 | Knute | |
| 5,503,728 A | 4/1996 | Kaneko et al. | |
| 5,505,828 A | 4/1996 | Wong et al. | |
| 5,512,159 A | 4/1996 | Yoshioka et al. | |
| 5,515,848 A | 5/1996 | Corbett, III et al. | |
| 5,609,749 A | 3/1997 | Yamauchi et al. | |
| 5,697,366 A | 12/1997 | Kimball et al. | |
| 5,720,862 A | 2/1998 | Hamamoto et al. | |
| 5,763,760 A | 6/1998 | Gumbrecht et al. | |
| 5,777,060 A | 7/1998 | Van Antwerp | |
| 5,814,601 A | 9/1998 | Winslow et al. | |
| 5,972,199 A | 10/1999 | Heller et al. | |
| 5,976,085 A | 11/1999 | Kimball et al. | |
| 6,027,445 A | 2/2000 | Von Bahr | |
| 6,051,389 A | 4/2000 | Ahl et al. | |
| 6,099,484 A | 8/2000 | Douglas et al. | |
| 6,104,940 A | 8/2000 | Watanabe et al. | |
| 6,117,290 A * | 9/2000 | Say | G01N 27/3271 204/403.1 |
| 6,128,519 A | 10/2000 | Say | |
| 6,349,229 B1 | 2/2002 | Watanabe et al. | |
| 6,464,849 B1 | 10/2002 | Say et al. | |
| 2004/0186408 A1 | 9/2004 | Behague et al. | |
| 2005/0238537 A1 | 10/2005 | Say et al. | |
| 2010/0252430 A1 | 10/2010 | Say et al. | |
| 2011/0266149 A1 | 11/2011 | Say | |

FOREIGN PATENT DOCUMENTS

| | | |
|---|---|---|
| EP | 0 420 296 A1 | 4/1991 |
| EP | 0 367 752 | 12/1993 |
| EP | 0 592 805 A2 | 4/1994 |
| EP | 0 710 835 A2 | 5/1996 |
| EP | 0 792 620 A2 | 9/1997 |
| WO | WO 94/21163 | 9/1994 |
| WO | WO 95/04928 | 2/1995 |
| WO | WO 96/06947 | 3/1996 |
| WO | WO 96/22730 | 8/1996 |
| WO | WO 97/15827 | 5/1997 |
| WO | WO 98/32013 | 7/1998 |
| WO | WO 2009/032760 | 3/2009 |
| WO | WO 2009/051901 | 4/2009 |

OTHER PUBLICATIONS

Supplemental Preliminary Amendment filed in the parent application having U.S. Appl. No. 11/002,718, filed Dec. 1, 2004, to Say et al.
U.S. Non-Final Office Action cited in U.S. Appl. No. 11/002,718 mailed May 1, 2008.
Amendment filed Nov. 3, 2008 in response to Office Action cited in U.S. Appl. No. 11/002,718.
U.S. Final Office Action cited in U.S. Appl. No. 11/002,718 mailed Jan. 23, 2009.
Amendment filed Jun. 23, 2009 in response to Office Action cited in U.S. Appl. No. 11/002,718.
U.S. Advisory Action cited in U.S. Appl. No. 11/002,718 mailed Jul. 10, 2009.
Amendment filed Jul. 22, 2009 in response to Office Action cited in Serial No. 002,718.
U.S. Non-Final Office Action cited in U.S. Appl. No. 11/002,718 mailed Oct. 5, 2009.
Jaraba, P. et al., "NADH amperometric sensor based on poly(3-methylthiophene)-coated cylindrical carbon fiber microelectrodes: application to the enzymatic determination of L-lactate," *Electrochimica Acta*, vol. 43, No. 23, pp. 3555-3565 (1998).
Netchiporouk, L. et al., "Properties of carbon fibre microelectrodes as a basis for enzyme biosensors," *Analytica Chimica Acta*, vol. 303, pp. 275-283 (1995).
Sakslund, H. et al., "Analysis of the factors determining the sensitivity of a miniaturized glucose biosensor made by codeposition of palladium and glucose oxidase onto an 8 µm carbon fiber," *Journal of Electroanalytical Chemistry*, vol. 402, pp. 149-160 (1996).
Sakslund, H. et al., "Development and evaluation of glucose microsensors based on electrochemical codeposition of ruthenium and glucose oxidase onto carbon fiber microelectrodes," *Journal of Electroanalytical Chemistry*, vol. 397, pp. 149-155 (1995).

* cited by examiner

FLUID MANAGEMENT AND PATIENT MONITORING SYSTEM

This application is a National Stage Application of PCT/US2012/038598, filed May 18, 2012, which claims priority to the U.S. Provisional Application Ser. No. 61/487,937 filed May 19, 2011, the subject matter of which is incorporated herein by reference in its entirety. To the extent appropriate, a claim of priority is made to each of the above disclosed applications.

TECHNICAL FIELD

The disclosure relates generally to systems and methods for measuring bioanalytes. More particularly, the present disclosure relates to systems and methods for measuring lactate.

BACKGROUND

For critical care patients, physicians have long relied on personal examination and clinical laboratory results to determine the presence and concentration of biological analytes in a patient. Clinical laboratories offer a wide range of automated systems for high-volume testing and analytical support in a well controlled, high quality environment. However, clinical laboratories can not provide the immediate results needed to properly treat trauma and multi organ dysfunction/failure patients.

To meet the clinical need for immediate test results, several technologies are emerging for testing using reliable, automated analyzers at the patient's bedside. This type of testing is commonly termed point-of-care (POC) diagnostic testing. POC diagnostic test systems include electrochemical biosensors, optical fluorescence sensors, paramagnetic particles for coagulation test systems, and micromachined devices for both chemical and immunochemical testing. These technologies have allowed multi-analyte chemistry panels to be performed rapidly and have addressed previous obstacles such as calibration of test devices. POC tests can be classified as: 1) in vitro, which is performed at the bedside; 2) ex vivo or para vivo, which is performed at wrist-side; and 3) in vivo, which is performed inside the patient. POC tests offer indirect cost efficiencies and savings such as reduced labor costs, decreased blood identification and transport errors, and reduced patient complications.

In vitro or bedside POC devices are used typically in several departments of the hospital including intensive care units; operating rooms; emergency departments (ER); interventional departments; general patient care departments; and outpatient surgery and ambulatory care units. In vitro POC diagnostic tests offer a wide range of diagnostic tests, similar to the clinical laboratory. In vitro POC diagnostic test systems typically are not connected on-line to the patient and require an operator for blood sampling. Key categories of diagnostic test in the POC diagnostic market include arterial blood gases, blood chemistries, blood glucose, coagulation, drugs-of-abuse testing, hemoglobin, hematocrit, infectious diseases, and therapeutic drug monitoring. Other categories include cancer markers, cardiac markers, cholesterol detection, immunodiagnostics, infectious disease detection, lactate, and thrombolytic monitoring.

Ex vivo POC diagnostics use external sensors for on-line real-time testing with little to no blood loss. Typically, sampled blood flows through a closed system to minimize blood contact. Ex vivo POC systems minimize problems associated with in vivo sensors, including clotting, inaccuracy, calibration drift, and an inability to recalibrate once in the patient. U.S. Pat. No. 5,505,828 discloses an exemplary ex vivo POC system.

In vivo POC diagnostics offer considerable potential in the treatment of most critical and unstable patients. Although many companies are developing in vivo sensors, technical hurdles have thus far kept in vivo sensors from common commercial use.

Ex vivo and in vivo POC diagnostics, since they are on-line systems, can reduce quality control and information integration errors that occur with clinical or in vitro POC tests. Quality control errors are commonly due to operator errors, not instrument errors or device failures. Exemplary errors include inappropriate specimen volume, inaccurate calibration, use of deteriorated test strips, inadequate validation, insufficient instrument maintenance, bad timing of the test procedure, and use of the wrong materials. Clinical information system integration allows test data collected at the bedside to be put directly into the patient record. This improves the efficiency of the patient management process, allowing the integration of the laboratory's information system and clinical information systems, providing a "seamless" flow of all types of patient information.

Although there exists a number of viable systems for determining blood lactate values, no current commercially available device can economically monitor patient trend lactate valued in near real time over a desired period of eight hours. This requirement is considered important to further ongoing research that increasingly suggests trend lactate monitoring will emerge as an important clinical standard in the critical care setting.

SUMMARY

The present disclosure relates generally to systems and methods for measuring bioanalytes. More particularly, the present disclosure relates to systems and methods for measuring lactate.

One aspect of the present disclosure relates to a fluid management system consisting of a pumping mechanism, a check valve, a reservoir, tubing, a sensor, and connective means for enabling either ex vivo or in vivo lactate monitoring by a clinician. This arrangement composes a disposable set assembly that is mounted by a clinician to a lactate monitor that in turn provides the data acquisition, storage and display functions. The disposable set assembly is designed for low cost injection molding and low volume, partially automated assembly by means of ultrasonic or laser welding. Sub-assemblies of the set may be fabricated using transfer adhesive films or U.V. curable epoxies.

Another aspect of the present disclosure relates to the pump device, which includes a housing defining a piston chamber (or cylinder) and a piston is reciprocally mounted within the chamber. The reciprocating motion of the piston results in a reciprocating flow of fluid within a single fluid line. The reciprocating flow provides a first cycle calibration and anticoagulant wash when caused to move a volume toward the patient as a result of a "push" direction of the piston, and wherein the directional control of fluid is by a "valve-less" means that uses the differential pressure gradient of two possible inlet ports accessing the piston cylinder. A second cycle in the opposite or "pull" direction causes a patient blood sample to be drawn over the sensor arrangement, where the blood analysis is taken, and wherein a check valve provides the directional control of the fluid.

A further aspect of the present disclosure relates to the calibrant as being a common infusion agent such as Ringers Lactate, and the anticoagulant being such as sodium citrate.

A further aspect of the present disclosure relates to a method of relating the fluid line component volumes with the sensor position, whereby the "pull" stroke of the piston in traversing the cylinder provides a complete volume needed to acquire a substantially pure sample of the patient blood and locate it over a working electrode of the sensor. Likewise, the "push" stroke of the piston in traversing the cylinder provides a complete volume needed to wash the analyzed blood components from the fluid line and position a substantially pure anticoagulant/calibrant mixture over the working electrode of the sensor. Importantly, the "push" stroke results in a volume of fluid moved that is greater than the "pull" stroke by an amount equal to the portion of the piston cylinder traversed that is located above the check valve. By controlling that portion of the cylinder length, an amount of fluid may be determined that is sufficient to flush the fluid system completely by pushing a defined quantity of anticoagulant/calibrant into the patient. Once defined and incorporated into the mechanism the possible volume that may be introduced is a novel, self-limiting feature, that prevents the patient from over or under infusion of the anticoagulant/calibrant mixture in the flush cycle. This feature eliminates positioning variability and chain of potential failure modes inherent in typical analogous systems using pumping mechanism drivers and software as the actuating mechanisms.

The system is so designed as to have inherent safety features, simplified set up, intuitive patient interface, and minimal total parts required for manufacture. Additional design goals are to reduce both cost and potential failure modes and to facilitate sterilization and packaging.

DETAILED DESCRIPTION

Reference will now be made in detail to exemplary aspects of the present disclosure which are illustrated in the accompanying drawings. Wherever possible, the same reference numbers will be used throughout the drawings to refer to the same or like parts.

An aspect of the present disclosure relates to systems and methods for providing on-line monitoring/measurement of bioanalytes in a patient. One particular aspect of the present disclosure relates to systems and methods for providing on-line measurement of lactate concentrations in a patient.

Lactate is a small molecule that is produced by all tissues and organs of a patient's body that are in "distress". When the demands for oxygen exceed the supply at a location in a patient's body, then a state of low perfusion exists and lactate is produced at the location. For example, lactate is produced if a patient is bleeding, if a patient's heart is failing, if a person's limb is in danger of being lost, or if a person is not getting enough oxygen to breathe. Thus, many life and limb threatening clinical states produce elevated blood lactate levels, even in the face of adequate oxygen delivery to the patient. It is a matter of oxygen supply and metabolic demand.

At the cellular level, lactate is inversely proportional to the vital cellular energy stores of adenosine triphosphate and is produced within six seconds of inadequate perfusion or cellular injury. It is thus an ideal biochemical monitor of cellular viability at the tissue level, and of patient viability at the systemic level.

Clinically, the dire significance of elevated and rising blood lactate values is known. Trauma physicians and clinical evidence support the hypothesis that a simple, inexpensive, continuous, monitor of lactate in the trauma setting will save lives by providing timely, life-saving information that will help dictate triage and therapy. For example, an emergency room patient who has a blood lactate level of 4 mM has a 92% mortality rate within the next 24 hours. If this level is 6 mM, then the mortality rate rises to 98%. In animal experiments, blood lactate levels begin to rise within minutes of hemorrhage, and conversely, begin to fall just as quickly with adequate resuscitation. In multivariate analysis, blood lactate is the best indicator of the degree of shock (superior to blood pressure, heart rate, urine output, base deficit, blood gas and Swan-Ganz data) and is proportional to the shed blood volume. Blood lactate levels correlate with a trauma patient's chances of survival. Therapy that fails to control a patient's increasing lactate levels must be modified or additional diagnoses quickly sought.

Figure 1A:
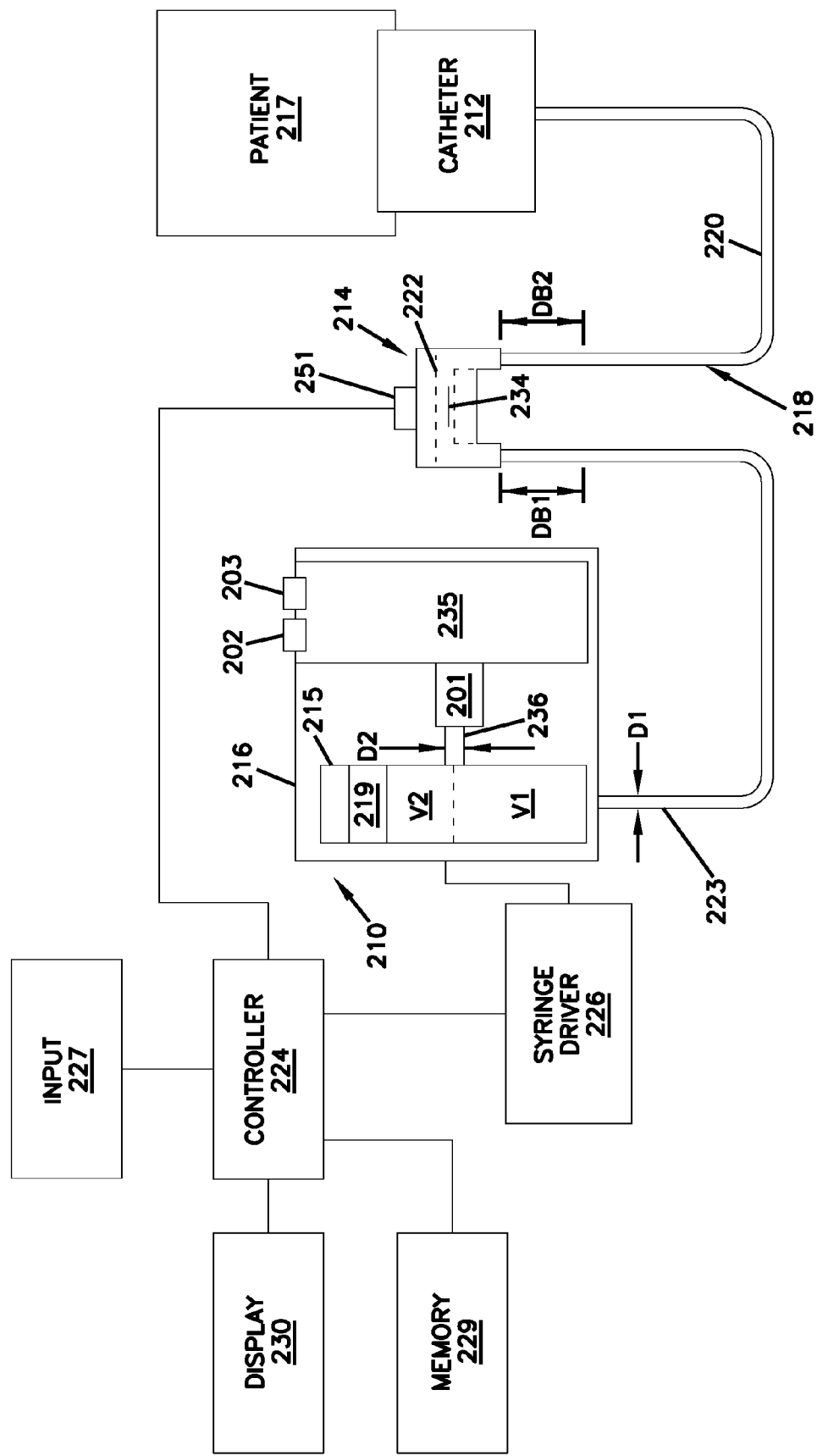
FIG. 1A is a schematic depiction of an embodiment of an ex vivo sensor system or arrangement constructed in accordance with the principles of the present disclosure.

FIG. 1A illustrates an example sensor system or arrangement 210 that is one example implementation of the present disclosure. The sensor system 210 generally includes a catheter 212 for withdrawing a test fluid sample, a sensor module 214 for measuring an analyte such as lactate in the sample, and a pump module 216 for controlling the fluid flow within the sensor system 210. In the example shown, the sensor module 214 is an ex vivo analyte sensor 214 for the on-line measurement of bioanalytes, such as lactate, glucose or other analytes.

Certain types of sensor modules 214 include an electrochemical sensor 234. In some implementations, the electrochemical sensor 234 of the sensor arrangement 210 is a sensor fiber for detecting or measuring bioanalytes. In other implementations, the electrochemical sensor 234 of the sensor arrangement 210 includes a plate sensor or other suitable sensor. Additional information pertaining to ex vivo sensors 214 can be found in U.S. Pat. No. 6,117,290, the disclosure of which is hereby incorporated herein by reference. In other implementations, the electrochemical sensor of the sensor arrangement 214' includes one or more sensor fibers for detecting or measuring bioanalytes.

To promote manufacturing and operational efficiency, certain implementations of the system 210 have a single uninterrupted flow path 218 adapted to extend from a patient 217, past an analyte sensor 214, to a pump module 216. The phrase "single uninterrupted flow path" is intended to mean that the system 210 does not use flow control devices to selectively provide and inhibit access between the pump module 216 and the patient 217. The flow path 218 is formed by a first flow line 220 extending between the catheter 212 and the sensor module 214, a test chamber 222 formed through the sensor module 214, and a second flow line 223 extending between the sensor module 214 and the pump module 216.

The pump module 216 includes a pump body 215 and a source of calibration fluid (a reservoir) 235. The pump body 215 and reservoir 235 are integral as described in more detail herein. The pump module 216 functions as a source of calibration fluid with respect to the single uninterrupted flow path 218 that extends between the pump module 216 and the catheter 212. The pump module 216 draws calibration fluid from the calibration fluid reservoir 235 through a flow line 236. In certain implementations, a check valve sub-assembly 201 is located at the flow line 236 to inhibit contamination of the calibration fluid in the reservoir 235.

Calibration fluid contained by the reservoir 235 includes a predetermined concentration of a calibrant. Some example calibrants include lactate for lactate sensors and glucose for glucose sensors. The calibration fluid can include a variety of other components in addition to a calibrant. For example, the calibrant fluid may contain an anticoagulant, such as sodium citrate. One example calibration fluid includes a solution of sodium citrate, saline, and lactate. Of course, lactate may be used as a calibrant if a lactate sensor is being used in the system. Other types of calibrant that may be used with other types of sensors include glucose, potassium, sodium, calcium, and ringers lactate.

The example system 210 is preferably a bi-directional system. The term "bidirectional" is intended to mean that fluid flow is directed back and forth across the sensor 214 through the single flow line 218. While certain implementations of the system 210 could utilize valves between the pump module 216 and the patient 217, the bi-directional nature of the system 210 eliminates the need for such internal valves along the continuous flow path. The bi-directional nature of the system 210 also reduces manufacturing costs. This cost reduction is particularly significant in disposable systems.

In operation, the pump module 216 can direct fluid flow in a first direction from the pump module 216 toward the patient 217. In particular, the pump module 216 directs calibration fluid from the pump module 216 past the sensor 214 at towards the patient 217. This fluid flow allows the sensor 214 to be calibrated and the entire flow path to be coated with anticoagulant. After calibration of the sensor 214 and coating of the flow path with anticoagulant, the pump module 216 reverses the flow in the system 210 to cause a fluid sample to flow from the patient 217 across the sensor 214 toward the pump module 216. This fluid flow allows an analyte level of the fluid sample to be measured by the sensor 214.

The reservoir 235 of the pump module 216 defines a first port and a second port. A fill septum 202 at the first port enables filling of the reservoir 235 with the anticoagulant/calibrant fluid mixture during manufacture. In certain implementations, a silicone rubber fill septum 202 may be located at the first port to enable ingress of calibration fluid without the need for a complex valve mechanism. An air vent 203 at the second port allows air to be displaced from a void within the reservoir 235 as the calibration fluid is added during manufacture. The air vent 203 also allows air to enter the reservoir 235 as the calibration fluid is depleted during the normal operation of the device. In certain implementations, a non-woven Teflon® vent 203 may be located at the second port to enable ingress/egress of ambient air into the reservoir 235.

The sensor system 210 also includes a control unit or controller 224 that operates the pump module 216. In certain implementations, the control unit 224 interfaces with a pump driver 226, the sensor 214 (via a connector 251), an input unit 227 (e.g., a keyboard), memory 229, and a display unit 230 (e.g., a monitor). It will be appreciated that the control unit 224 can include any type of controller, such as a micro-controller, a mechanical controller, an electrical controller, a hardware-driven controller, a firmware-driven controller, or a software-driven controller. Similarly, the pumping mechanism driver 226, display unit 230, and the input unit 227 can include off-the-shelf components. For example, a suitable device incorporating a controller, a display unit, an input unit, and a pumping mechanism driver is sold by Alaris Corporation of San Diego, Calif. under the name Ivac®, or by Medex Corporation of Hilliard, Ohio under the name MedFusion®.

In some implementations, the first and second flow lines 220, 223 are formed by conventional medical tubing. In certain embodiments, the first and second flow lines 220, 223 have relatively small diameters that inhibit mixing between fluid samples drawn through the catheter 212 and calibration fluid dispensed into the flow path 218 through the pump module 216. Mixing also is inhibited because the dynamic frontier formed between the fluid sample and the calibration fluid has a small area so that contamination by diffusion is minimized. Additionally, mixing is also inhibited by maintaining laminar flow within the flow path 218.

In certain embodiments, the flow lines 220 and 223 have inner diameters less than about ⅛ inches. In certain embodiments, the flow lines 220 and 223 have inner diameters less than about 0.1 inches. In certain embodiments, the flow lines 220 and 223 have inner diameters of about 0.010 inches. In certain embodiments, the flow lines 220 and 223 have inner diameters of between about 0.002 inches to about 0.015 inches. In certain embodiments, the flow lines 220 and 223 have inner diameters of between about 0.005 inches to about 0.010 inches. In another example implementation, the flow lines 220 and 223 have inner diameters of about 0.005 inches. In one example implementation, the flow lines 220 and 223 have inner diameters of about 0.006 inches. In another example implementation, the flow lines 220 and 223 have inner diameters of about 0.007 inches. In another example implementation, the flow lines 220 and 223 have inner diameters of about 0.008 inches. In another example implementation, the flow lines 220 and 223 have inner diameters of about 0.009 inches.

In accordance with some aspects, a diameter D1 of the second flow line 223 is less than a diameter D2 of a flow line 236 leading to the check-valve 201. In some implementations, the diameter D1 of the second flow line 223 is significantly less than the diameter D2 of the flow line 236 to the check-valve 201. When the pump body 215 is creating fluid flow in the second direction, the pump body 215 is applying a suction pressure at the check valve 201 and at the second flow line 223. However, due to the difference in diameters D1, D2, the calibration fluid enters the pump body 215 from the reservoir 235 instead of the fluid from the second flow line 223.

In some implementations, the diameter D2 of the flow passage 236 to the check-valve 201 is at least 1.5 times the size of the diameter D1 of the second flow line 223. In certain implementations, the diameter D2 of the flow passage 236 to the check-valve 201 is about twice the size of the diameter D1 of the second flow line 223. In certain implementations, the diameter D2 of the flow passage 236 to the check-valve 201 is about three times the size of the diameter D1 of the second flow line 223. In certain implementations, the diameter D2 of the flow passage 236 to the check-valve 201 is about four times the size of the diameter D1 of the second flow line 223. In certain implementations, the diameter D2 of the flow passage 236 to the check-valve 201 is about five times the size of the diameter D1 of the second flow line 223.

In some implementations, the diameter D2 of the check-valve passage 236 is at least 0.01 inches. Indeed, in some implementations, the diameter D2 is at least 0.02 inches. In certain implementations, the diameter D2 is about 0.025 inches. In certain implementations, the diameter D2 is between about 0.03 inches and about 0.06 inches. In certain implementations, the diameter D2 is about 0.03 inches. In certain implementations, the diameter D2 is about 0.04 inches. In certain implementations, the diameter D2 is about 0.05 inches. In certain implementations, the diameter D2 is about 0.06 inches. In other implementations, the diameter D2 may be larger than 0.06 inches.

In accordance with some aspects, a transverse cross-sectional area of the second flow line 223 is less than a transverse cross-sectional area of the passage through the check-valve 201 between the reservoir 235 and the pump body 215. In some implementations, the transverse cross-sectional area of the second flow line 223 is significantly less than the transverse cross-sectional area of the check-valve 201. When the pump body 215 is creating fluid flow in the second direction, the pump body 215 is applying a suction pressure at the check valve 201 and at the second flow line 223. However, due to the difference in transverse cross-sectional areas, the calibration fluid enters the pump body 215 from the reservoir 235 instead of the fluid from the second flow line 223.

In some implementations, the transverse cross-sectional area of the flow passage 236 to the check-valve 201 is at least twice the size of the transverse cross-sectional area of the second flow line 223. In certain implementations, the transverse cross-sectional area of the flow passage 236 to the check-valve 201 is about three times the size of the transverse cross-sectional area of the second flow line 223. In certain implementations, the transverse cross-sectional area of the flow passage 236 to the check-valve 201 is about five times the size of the transverse cross-sectional area of the second flow line 223. In certain implementations, the transverse cross-sectional area of the flow passage 236 to the check-valve 201 is about ten times the size of the transverse cross-sectional area of the second flow line 223. In other implementations, the transverse cross-sectional area of the flow passage 236 sufficiently larger than the transverse cross-sectional area of the second flow line 223 to produce flow at only the flow passage 236 when suction is applied to both.

In accordance with some aspects, the port for the check valve subassembly 201 divides the pump body 215 into a first volume V1 and a second volume V2. The first volume V1 refers to the internal volume of the pump body 215 between the check valve port and a liquid interface surface of a piston 219 when the piston 219 is located at a lower-most point within the pump body 215. The second volume V2 refers to the internal volume of the pump body 215 between the check valve port and the liquid interface surface of the piston 219 when the piston 219 is located at an upper-most point within the pump body 215.

When a piston 219 of the pump body 215 is located in the first volume V1, the piston 219 blocks the flow line 236 to the reservoir 235. Accordingly, movement of a piston 219 within the first volume V1 of the pump body 215 towards the second volume V2 does not apply a suction pressure to the reservoir flow line 236. Rather, such a movement of the piston 219 applies a suction pressure to the second flow line 223, thereby causing a fluid sample to be withdrawn from the patient 217. Continued movement of the piston 219 into the second volume V2 of the pump body 215 unblocks the reservoir flow line 236. As noted above, the difference in size between the check valve port and the second flow line 223 causes the continued movement of the piston 219 to pull calibration fluid into the pump body 215 from the reservoir 235 instead of continuing to pull the fluid sample from the patient 217. Moving the piston 219 back towards the first volume V1 pushes the calibration fluid from the pump body 215 into the second flow line 223 towards the sensor 214. The calibration fluid pushes the fluid sample from the sensor 214 back towards the patient 217.

The calibration fluid mixes with the withdrawn fluid sample to a limited extent at a region where the two fluids meet. Fresh calibration fluid from the reservoir 4 mixes with spent calibration fluid to a limited extent at a region where the two fluids meet. As noted above, the dimensions of the flow lines 220, 223 inhibit mixing of fluids. Accordingly, any mixing occurs over a limited length of the flow line 220, 223 known as a diffusion barrier. The length over which such barriers extend will depend on the concentration of the fluids, the duty cycle of the pump module 216, the size of the flow lines 220, 223, as well as other factors. A first diffusion barrier DB1 refers to a length beyond which the blood sample cannot diffuse into the calibration fluid. A second diffusion barrier DB2 refers to a length beyond which fresh calibration fluid cannot diffuse into the spent calibration fluid.

In some implementations, the pump module 216 initiates a duty cycle of the sensor system 210 by washing the sensor 214 and flow lines 223, 220 in calibration fluid. In some implementations, the pump module 216 first moves in a "pull" direction through the second volume V2 of the pump body 215 to draw fresh calibration fluid into the pump body 215. In other implementations, the pump module 216 previously drew in fresh calibration fluid at the end of the previous duty cycle. The pump module 216 moves in a "push" direction to expel the calibration fluid. In some implementations, the pump module 216 expels sufficient calibration fluid to coat at least the first flow line 223 and the test chamber 222 of the sensor 214. In certain implementations, the pump module 216 expels sufficient calibration fluid to also coat at least part of the first flow line 220. In one implementation, the pump module 216 expels sufficient calibration fluid to coat the entire first flow line 220. After calibrating the sensor 214, the pump module 216 moves in the "pull" direction draws a blood sample from the patient towards the sensor 214 for analysis.

When the piston 219 of the pump module 216 moves in the "push" direction towards the lower-most point within the pump body 215, the piston 219 pushes the fresh calibration fluid from the pump body 215 into the second flow line 223. In some implementations, the second volume V2 of the pump body 215 is at least as large as a total volume of the second flow line 223 and the test chamber 222. In certain implementations, the second volume V2 of the pump body 215 is at least as large as the total volume of the second flow line 223, the test chamber 222, and the second diffusion barrier DB2. In such implementations, the pump 216 will expel sufficient fresh calibration fluid to wash these areas so that spent calibrant will not interfere with the sensor readings during calibration. In one implementation, the second volume V2 of the pump body 215 is as large as the total volume of the second flow line 223, the test chamber 222, and the first flow line 220. In such implementations, the pump module 216 expels sufficient fresh calibration fluid to purge all spent calibrant from the flow line and into the patient.

When the piston 219 of the pump module 216 moves along the first volume V1 of the pump body 215 in the "pull" direction, the piston 219 draws a blood sample from the patient 217 into the first flow line 220. In some implementations, the first volume V1 of the pump body 215 is at least as large as a total volume of the first flow line 220 and the test chamber 222. In certain implementations, the first volume V1 of the pump body 215 is at least as large as a total volume of the first flow line 220, the sensor test chamber 222, and the first diffusion barrier DB1. In such implementations, the pump 216 will pull a sufficient volume of blood to flush the sensor test chamber 222 of calibrant before analyzing the blood sample, thereby enhancing the accuracy of the test analysis. As noted above, continued movement of the piston 219 through the second volume V2 in the "pull" direction causes the second volume V2 of the pump body 215 to fill with fresh calibration fluid.

To minimize patient discomfort, another aspect of the disclosure relates to using relatively low flow rates through the flow path. In some implementations, the catheter 212 is a relatively small diameter catheter capable of withdrawing blood samples from a capillary bed of a patient 217. In certain implementations, the catheter 212 is capable of withdrawing blood or other fluid samples at a rate less than 100 microliters per minute. Indeed, in certain implementations, the catheter 212 is capable of withdrawing blood or other fluid samples at a rate less than 50 microliters per minute. Such low flow rates enable sample fluids to be drawn from low flow regions, such as capillary beds, thereby further reducing patient discomfort. Of course, conventional venous catheters and other types of catheters also can be utilized for withdrawing test fluids from a patient. In other implementations, other techniques for withdrawing fluid samples from a patient in medical applications (e.g., intracranial pressure (ICP), microdialysis and iontophoresis) also may be utilized.

The general system 210 described above provides a simple and relatively inexpensive system for monitoring analyte levels, such as lactate levels, in a patient. Because the system 210 has a minimal number of parts, the system is suited for disposability. The simplicity of the system 210 also facilitates assembly and operation of the system.

Figure 1B:
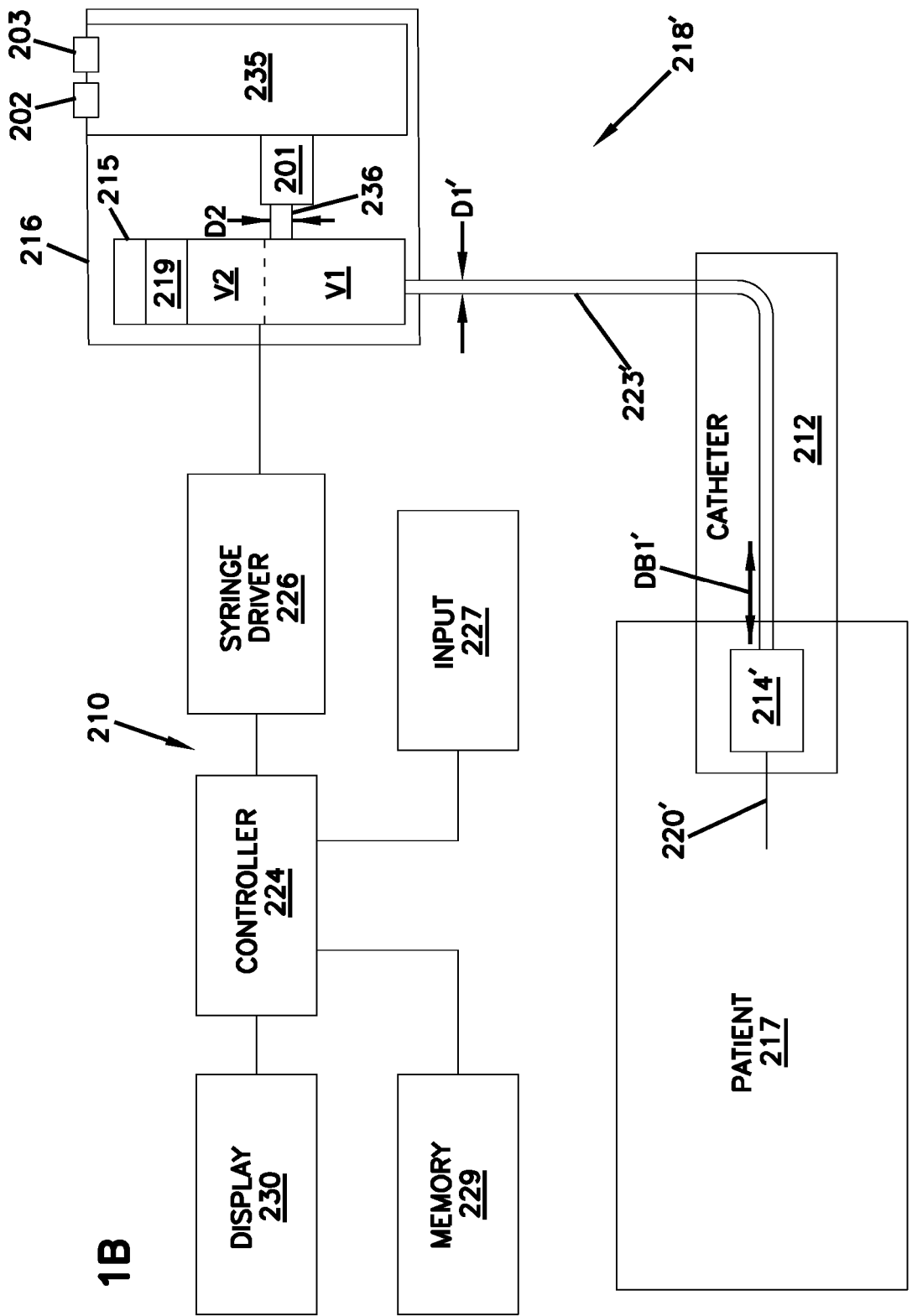
FIG. 1B is a schematic depiction of an embodiment of an in vivo sensor system or arrangement constructed in accordance with the principles of the present disclosure.

FIG. 1B illustrates another example sensor system or arrangement 210' providing an in vivo analyte sensor for the on-line measurement of bioanalytes, such as lactate, glucose or other analytes. The sensor system 210' generally includes a catheter 212 for withdrawing a test fluid sample, an in vivo sensor module 214' for measuring an analyte, and a pump module 216 for controlling the fluid flow within the sensor system 210. In the example shown, the example sensor arrangement 210' includes the same or similar pump module 216 as the sensor system 210 of FIG. 1A. In other implementations, other types of pumps may be utilized. In the example shown, the sensor arrangement 210' also includes the control unit or controller 224 that operates the pump module 216, the pump driver 226, the input unit 227 (e.g., a keyboard), the memory 229, and the display unit 230 (e.g., a monitor) of the sensor system 210 of FIG. 1A.

The sensor 214' includes an electrochemical sensor. Additional information pertaining to in vivo sensors 214' can be found in U.S. Publication No. 2010/0252430 to Say et al., the disclosure of which is hereby incorporated herein by reference. In some implementations, the electrochemical sensor of the sensor arrangement 214' includes one or more sensor fibers for detecting or measuring bioanalytes. In one example implementation, the sensor fiber includes a composite sensor fiber having a dielectric core, a conductive layer, and a sensing layer.

Some example sensor fibers are described in U.S. Pat. Nos. 5,264,105; 5,356,786; 5,262,035; and 5,320,725, the disclosures of which are incorporated by reference herein. Further examples of sensor fibers are described in U.S. application Ser. No. 13/129,325, filed May 13, 2011, and titled "Electrochemical Sensor Module," the disclosure of which is incorporated by reference herein. Other examples of sensor fibers are described in PCT Publication Nos. WO 2009/032760, and WO 2009/051901, the disclosures of which are incorporated by reference herein. In other implementations, the electrochemical sensor of the sensor arrangement 214' may include a plate sensor or other suitable sensor.

To promote manufacturing and operational efficiency, certain implementations of the system 210' have a single uninterrupted flow path 218' adapted to extend from a patient 217, past the in vivo analyte sensor 214', to a pump module 216. The phrase "single uninterrupted flow path" is intended to mean that the system 210' does not use flow control devices to selectively provide and inhibit access between the pump module 216 and the patient 217. The flow path 218' is formed by a first flow line 220' extending between the patient 217 and the sensor module 214', a test chamber 222 formed in the sensor module 214', and a second flow line 223 extending between the sensor module 214' and the pump module 216. The pump module 216 functions as a source of calibration fluid with respect to the single uninterrupted flow path 218' that extends between the pump module 216 and the patient 217.

As noted above, calibration fluid contained by the reservoir 235 of the pump module 216 includes a predetermined concentration of a calibrant. Some example calibrants include lactate for lactate sensors and glucose for glucose sensors. The calibration fluid can include a variety of other components in addition to a calibrant. For example, the calibrant fluid may contain an anticoagulant, such as sodium citrate. One example calibration fluid includes a solution of sodium citrate, saline, and lactate. Of course, lactate may be used as a calibrant if a lactate sensor is being used in the system. Other types of calibrant that may be used with other types of sensors include glucose, potassium, sodium, calcium, and ringers lactate.

The example system 210' is preferably a bi-directional system. The term "bidirectional" is intended to mean that fluid flow is directed back and forth across the in vivo sensor 214' through the single flow line 218'. While certain implementations of the system 210' could utilize valves between the pump module 216 and the patient 217, the bi-directional nature of the system 210' eliminates the need for such internal valves along the continuous flow path. The bi-directional nature of the system 210' also reduces manufacturing costs. This cost reduction is particularly significant in disposable systems.

In operation, the pump module 216 can direct fluid flow in a first direction from the pump module 216 toward the patient 217. In particular, the pump module 216 directs calibration fluid from the pump module 216 past the in vivo sensor 214' at towards the patient 217. This fluid flow allows the sensor 214' to be calibrated and the entire flow path to be coated with anticoagulant. After calibration of the sensor 214' and coating of the flow path with anticoagulant, the pump module 216 reverses the flow in the system 210 to cause a fluid sample to flow from the patient 217 across the sensor 214' toward the pump module 216. This fluid flow allows an analyte level of the fluid sample to be measured by the sensor 214'.

In some implementations, the first and second flow lines 220', 223' are formed by conventional medical tubing. In certain embodiments, the first and second flow lines 220', 223' have relatively small diameters that inhibit mixing between fluid samples and calibration fluid dispensed into the flow path 218' through the pump module 216. Mixing also is inhibited because the dynamic frontier formed between the fluid sample and the calibration fluid has a small area so that contamination by diffusion is minimized. Additionally, mixing is also inhibited by maintaining laminar flow within the flow path 218'.

In some implementations, the first flow line 220' has a relatively small diameter catheter capable of withdrawing blood samples from a capillary bed of a patient 217. In other implementations, the first flow line 220' has a larger diameter. In certain embodiments, the second flow line 223' has an inner diameter less than about ⅛ inches. In certain embodiments, the second flow line 223' has an inner diameter less than about 0.1 inches. In certain embodiments, the second flow line 223' has an inner diameter of about 0.010 inches. In certain embodiments, the second flow line 223' has an inner diameter of between about 0.002 inches to about 0.015 inches. In certain embodiments, the second flow line 223' has an inner diameter of between about 0.005 inches to about 0.010 inches. In another example implementation, the second flow line 223' has an inner diameter of about 0.005 inches. In one example implementation, the second flow line 223' has an inner diameter of about 0.006 inches. In another example implementation, the second flow line 223' has an inner diameter of about 0.007 inches. In another example implementation, the second flow line 223' has an inner diameter of about 0.008 inches. In another example implementation, the second flow line 223' has an inner diameter of about 0.009 inches.

In accordance with some aspects, a diameter D1' of the second flow line 223' is less than a diameter D2 of a flow line 236 leading to the check-valve 201 of the pump module 216. In some implementations, the diameter D1' of the second flow line 223' is significantly less than the diameter D2 of the flow line 236' to the check-valve 201. As disclosed above, when the pump body 215 is creating fluid flow in the second direction, the pump body 215 is applying a suction pressure at the check valve 201 and at the second flow line 223'. However, due to the difference in diameters D1', D2, the calibration fluid enters the pump body 215 from the reservoir 235 instead of the fluid from the second flow line 223'.

In some implementations, the diameter D2 of the flow passage 236 to the check-valve 201 is at least twice the size of the diameter D1' of the second flow line 223'. In certain implementations, the diameter D2 of the flow passage 236 to the check-valve 201 is about three times the size of the diameter D1' of the second flow line 223'. In certain implementations, the diameter D2 of the flow passage 236 to the check-valve 201 is about four times the size of the diameter D1' of the second flow line 223'. In certain implementations, the diameter D2 of the flow passage 236 to the check-valve 201 is about five times the size of the diameter D1' of the second flow line 223'. In certain implementations, the diameter D2 of the flow passage 236 to the check-valve 201 is about six times the size of the diameter D1' of the second flow line 223'. In other implementations, the diameter D2 may be about ten times the diameter D1'.

In some implementations, the diameter D2 of the check-valve passage 236 is at least 0.01 inches. Indeed, in some implementations, the diameter D2 is at least 0.02 inches. In certain implementations, the diameter D2 is about 0.025 inches. In certain implementations, the diameter D2 is between about 0.03 inches and about 0.06 inches. In certain implementations, the diameter D2 is about 0.03 inches. In certain implementations, the diameter D2 is about 0.04 inches. In certain implementations, the diameter D2 is about 0.05 inches. In certain implementations, the diameter D2 is about 0.06 inches. In other implementations, the diameter D2 may be larger than 0.06 inches.

In accordance with some aspects, a transverse cross-sectional area of the second flow line 223' is less than a transverse cross-sectional area of the passage through the check-valve 201 between the reservoir 235 and the pump body 215. In some implementations, the transverse cross-sectional area of the second flow line 223' is significantly less than the transverse cross-sectional area of the check-valve 201. When the pump body 215 is creating fluid flow in the second direction, the pump body 215 is applying a suction pressure at the check valve 201 and at the second flow line 223'. However, due to the difference in transverse cross-sectional areas, the calibration fluid enters the pump body 215 from the reservoir 235 instead of the fluid from the second flow line 223'.

In some implementations, the transverse cross-sectional area of the flow passage 236 to the check-valve 201 is at least twice the size of the transverse cross-sectional area of the second flow line 223'. In certain implementations, the transverse cross-sectional area of the flow passage 236 to the check-valve 201 is about three times the size of the transverse cross-sectional area of the second flow line 223'. In certain implementations, the transverse cross-sectional area of the flow passage 236 to the check-valve 201 is about four times the size of the transverse cross-sectional area of the second flow line 223'. In certain implementations, the transverse cross-sectional area of the flow passage 236 to the check-valve 201 is about five times the size of the transverse cross-sectional area of the second flow line 223'. In certain implementations, the transverse cross-sectional area of the flow passage 236 to the check-valve 201 is about six times the size of the transverse cross-sectional area of the second flow line 223'. In other implementations, the transverse cross-sectional area of the flow passage 236 may be about ten times the transverse cross-sectional area of the second flow line 223'.

In accordance with some aspects, the port for the check valve subassembly 201 divides the pump body 215 into a first volume V1 and a second volume V2. The first volume V1 refers to the internal volume of the pump body 215 between the check valve port and a liquid interface surface of a piston 219 when the piston 219 is located at a lower-most point within the pump body 215. The second volume V2 refers to the internal volume of the pump body 215 between the check valve port and the liquid interface surface of the piston 219 when the piston 219 is located at an upper-most point within the pump body 215.

When a piston 219 of the pump body 215 is located in the first volume V1, the piston 219 blocks the flow line 236 to the reservoir 235. Accordingly, movement of a piston 219 within the first volume V1 of the pump body 215 towards the second volume V2 does not apply a suction pressure to the reservoir flow line 236. Rather, such a movement of the piston 219 applies a suction pressure to the second flow line 223', thereby causing a fluid sample to be withdrawn from the patient 217. Continued movement of the piston 219 into the second volume V2 of the pump body 215 unblocks the reservoir flow line 236. As noted above, the difference in size between the check valve port and the second flow line 223' causes the continued movement of the piston 219 to pull calibration fluid into the pump body 215 from the reservoir 235 instead of continuing to pull the fluid sample from the patient 217. Moving the piston 219 back towards the first volume V1 pushes the calibration fluid from the pump body 215 into the second flow line 223' towards the sensor 214'. The calibration fluid pushes the fluid sample from the sensor 214' back towards the patient 217.

The calibration fluid mixes with the withdrawn fluid sample to a limited extent at a region where the two fluids meet. Fresh calibration fluid from the reservoir 4 mixes with spent calibration fluid to a limited extent at a region where the two fluids meet. As noted above, the dimensions of the flow lines 220', 223' inhibit mixing of fluids. Accordingly, any mixing occurs over a limited length of the flow line 220', 223' known as a diffusion barrier. The length over which such barriers extend will depend on the concentration of the fluids, the duty cycle of the pump module 216, the size of the flow lines 220', 223', as well as other factors. A first diffusion barrier DB1' refers to a length beyond which the blood sample cannot diffuse into the calibration fluid. A second diffusion barrier refers to a length beyond which fresh calibration fluid cannot diffuse into the spent calibration fluid. Because of the position of the in vivo sensor 214' and size of the first flow line 220, the second diffusion barrier is extremely short and, consequently, is not shown.

In some implementations, the pump module 216 initiates a duty cycle of the sensor system 210' by washing the sensor 214' and flow lines 223', 220' in calibration fluid. In some implementations, the pump module 216 first moves in a "pull" direction through the second volume V2 of the pump body 215 to draw fresh calibration fluid into the pump body 215. In other implementations, the pump module 216 previously drew in fresh calibration fluid at the end of the previous duty cycle. The pump module 216 moves in a "push" direction to expel the calibration fluid. In some implementations, the pump module 216 expels sufficient calibration fluid to coat at least the first flow line 223' and the test chamber 222 of the sensor 214'. In certain implementations, the pump module 216 expels sufficient calibration fluid to also coat at least part of the first flow line 220'. In one implementation, the pump module 216 expels sufficient calibration fluid to coat the entire first flow line 220'. After calibrating the sensor 214', the pump module 216 moves in the "pull" direction draws a blood sample from the patient towards the sensor 214' for analysis.

When the piston 219 of the pump module 216 moves in the "push" direction towards the lower-most point within the pump body 215, the piston 219 pushes the fresh calibration fluid from the pump body 215 into the second flow line 223'. In some implementations, the second volume V2 of the pump body 215 is at least as large as a total volume of the second flow line 223' and the test chamber 222. In one implementation, the second volume V2 of the pump body 215 is as large as the total volume of the second flow line 223', the test chamber 222, and the first flow line 220'. In such an implementation, the pump module 216 expels sufficient fresh calibration fluid to purge all spent calibrant from the flow line and into the patient.

In certain implementations, the second volume V2 of the pump body 215 is at least as large as the total volume of the second flow line 223', the test chamber 222, and the second diffusion barrier DB2'. In such implementations, the pump 216 will expel sufficient fresh calibration fluid to wash these areas so that spent calibrant will not interfere with the sensor readings during calibration. As noted above, the first flow line 220' and the second diffusion barrier are significantly shorter in sensor system 210' than they were in sensor system 210. Accordingly, the second volume V2 of the pump body 215 in sensor system 210' may be significantly smaller than the second volume V2 of the pump body 215 in sensor system 210.

When the piston 219 of the pump module 216 moves along the first volume V1 of the pump body 215 in the "pull" direction, the piston 219 draws a blood sample from the patient 217 into the first flow line 220'. In some implementations, the first volume V1 of the pump body 215 is at least as large as a total volume of the first flow line 220' and the test chamber 222. In certain implementations, the first volume V1 of the pump body 215 is at least as large as a total volume of the first flow line 220', the sensor test chamber 222, and the first diffusion barrier DB1'. In such implementations, the pump 216 will pull a sufficient volume of blood to flush the sensor test chamber 222 of calibrant before analyzing the blood sample, thereby enhancing the accuracy of the test analysis. As noted above, continued movement of the piston 219 through the second volume V2 in the "pull" direction causes the second volume V2 of the pump body 215 to fill with fresh calibration fluid.

To minimize patient discomfort, another aspect of the disclosure relates to using relatively low flow rates through the flow path. In certain implementations, the catheter 212 is capable of withdrawing blood or other fluid samples at a rate less than 100 microliters per minute. Indeed, in certain implementations, the catheter 212 is capable of withdrawing blood or other fluid samples at a rate less than 50 microliters per minute. Such low flow rates enable sample fluids to be drawn from low flow regions, such as capillary beds, thereby further reducing patient discomfort. Of course, conventional venous catheters and other types of catheters also can be utilized for withdrawing test fluids from a patient. In other implementations, other techniques for withdrawing fluid samples from a patient in medical applications (e.g., intracranial pressure (ICP), microdialysis and iontophoresis) also may be utilized.

The general system 210' described above provides a simple and relatively inexpensive system for monitoring analyte levels, such as lactate levels, in a patient. Because the system 210' has a minimal number of parts, the system is suited for disposability. The simplicity of the system 210' also facilitates assembly and operation of the system.

Figure 2:
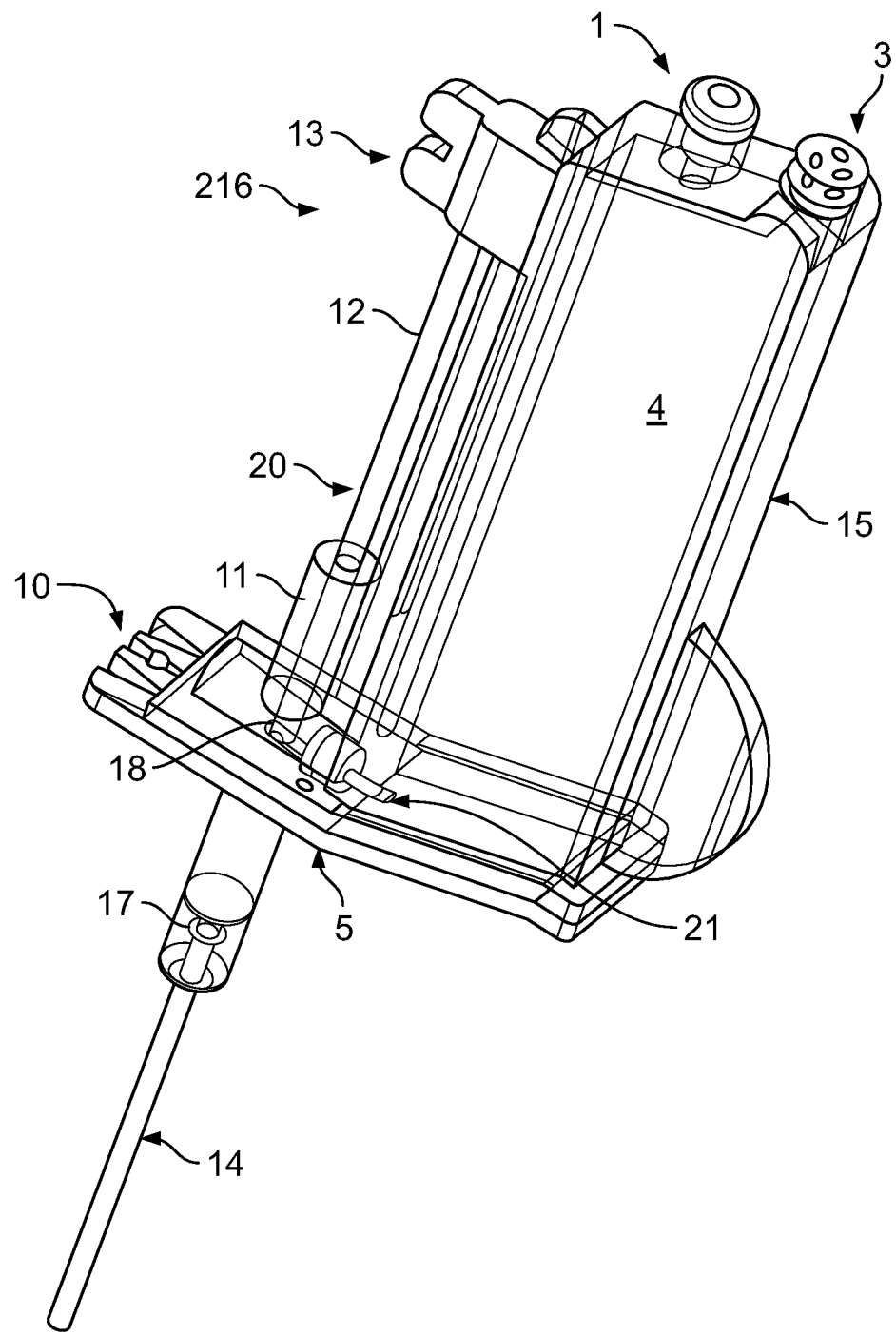
FIG. 2 is a perspective view of an example pump module suitable for use in the sensor systems of FIGS. 1A and 1B constructed in accordance with the principles of the present disclosure.
Figure 3:
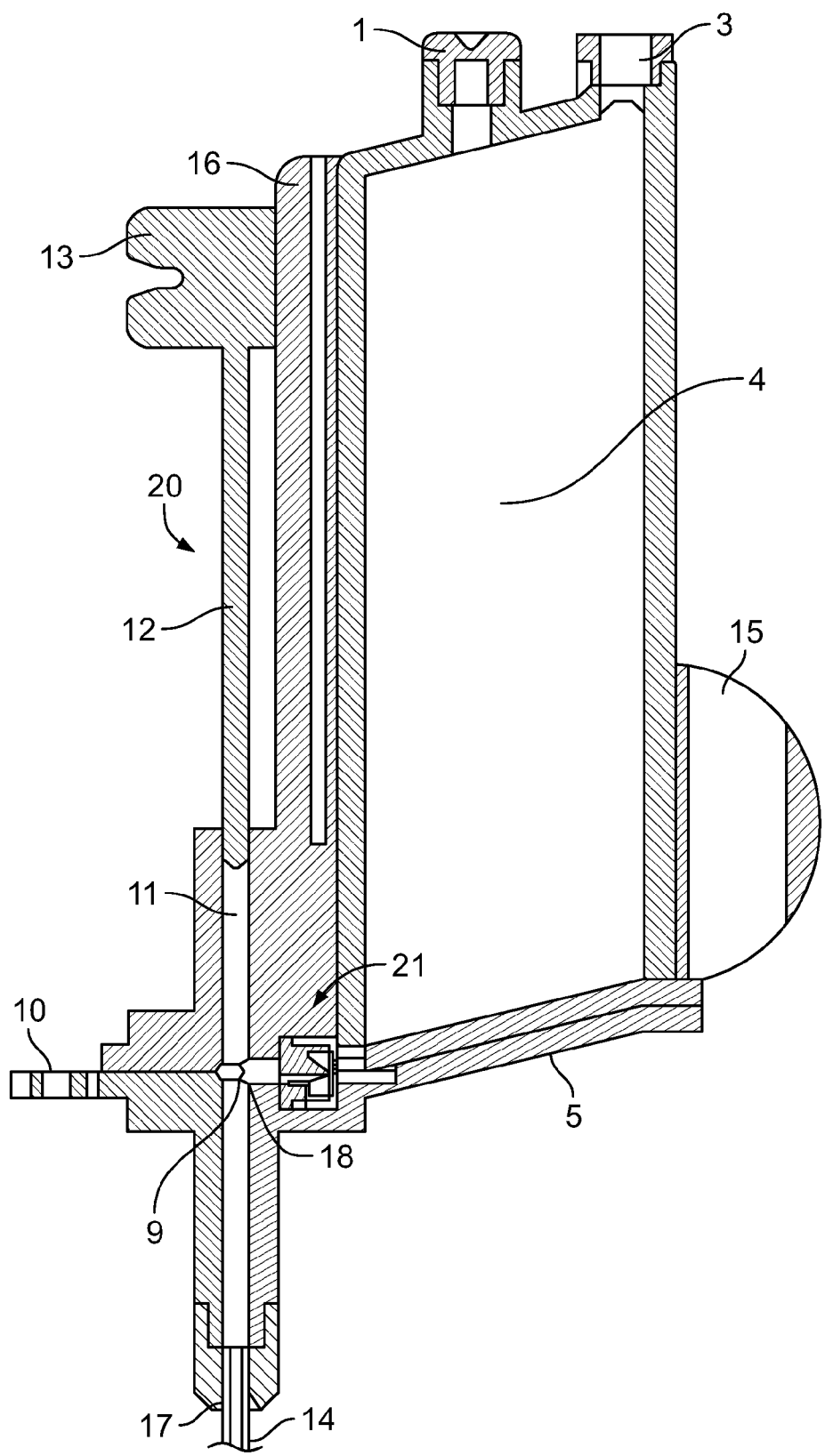
FIG. 3 is a schematic depiction of the pump module of FIG. 2.

FIGS. 2 and 3 illustrate one example implementation of a pump module 216 suitable for use with any sensor system described herein. The example pump module 216 includes a pumping mechanism 20, a check valve 21 (FIG. 6), and reservoir 4. The reservoir 4 holds a calibration fluid including calibrant. For example, in some implementations, the calibration fluid may contain Ringers Lactate or other such infusion agents). In certain implementations, the calibration fluid includes an anticoagulant, such as sodium citrate.

Figure 4:
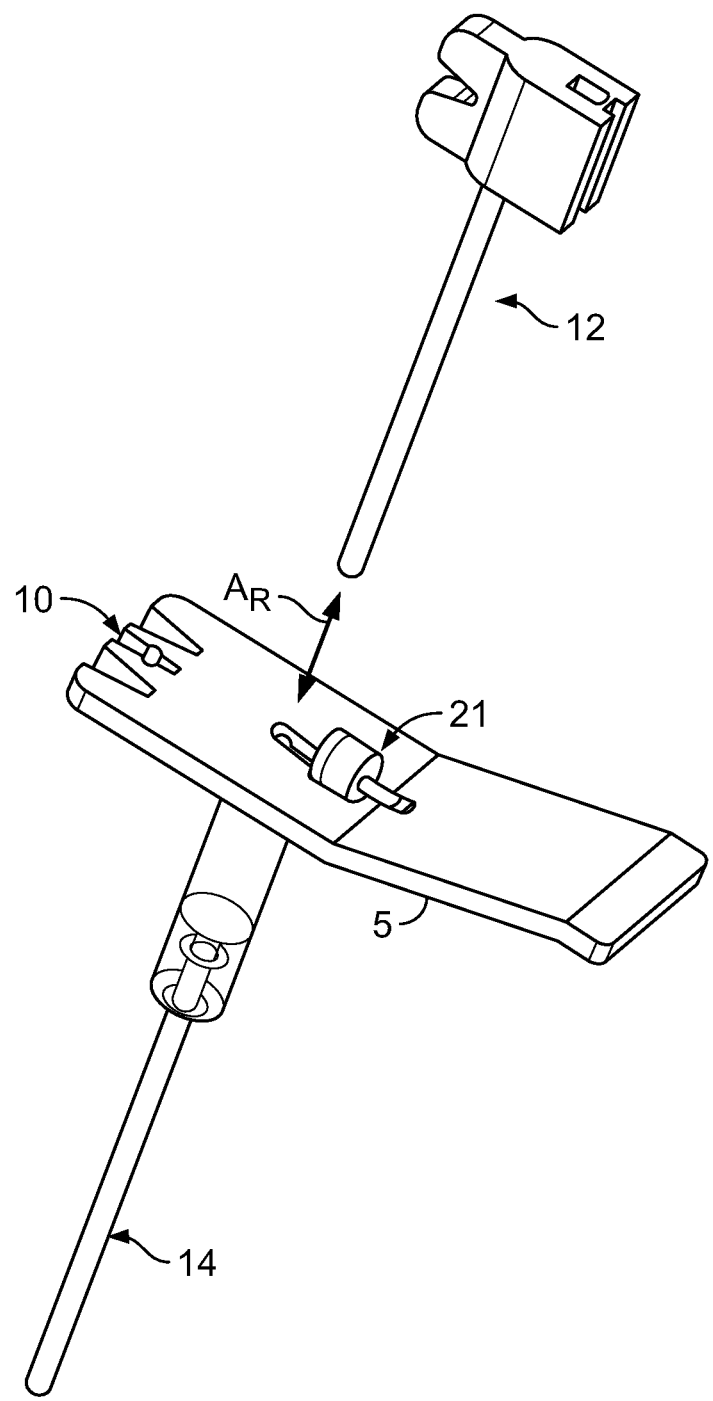
FIG. 4 is a perspective view of a portion of the pump module of FIG. 2 with a piston exploded from the bottom housing of the pump module.

In some implementations, the pump module 216 includes a sterilizable housing enclosing the pumping mechanism 20, the check valve 21, and the reservoir 4. In certain implementations, the housing includes a first housing part 5 and a second housing part 15 that are secured together. In the example shown, the first housing part 5 is a lower housing that defines part of the pumping mechanism 20 (see FIG. 4) and the second housing part 15 is an upper housing that defines the reservoir 4 and another part of the pumping mechanism 20 (FIG. 2). In other implementations, an integral pumping mechanism 20 can be coupled to an integral reservoir 4. In still other implementations, the reservoir 4 may be spaced from the pumping mechanism 20 as shown in U.S. Pat. No. 6,117,290, incorporated by reference above. Tubing 14 leads from the pumping mechanism 20 to a sensor (e.g., sensor 214 of FIG. 1A or sensor 214' of FIG. 1B).

In some implementations, the pump module 216 is disposable. In certain implementations, the tubing 14 also is disposable. Indeed, in certain implementations, the pump module 216, the tubing 14, and an analyte sensor (e.g., the ex vivo sensor 214 of FIG. 1A or the in vivo sensor 214' of FIG. 1B) form a disposable set assembly. A clinician connects the disposable assembly to a lactate monitoring system (e.g., see the controller 224 and other system components of FIGS. 1A and 1B) that, in turn, provides the data acquisition, storage, and display functions.

In certain implementations, the disposable set assembly is designed for low cost injection molding and low volume, partially automated assembly by means of ultrasonic or laser welding. Sub-assemblies of the set may be fabricated using transfer adhesive films or U.V. curable epoxies. In some implementations, the tubing 14 includes a 90/10 micro bore tubing. In other implementations, other types and sizes of tubing 14 may be utilized.

The pumping mechanism 20 includes a pump body defining an interior 11 in which fluid may be contained. In some implementations, the pump body interior 11 is divided into a first portion formed by the first housing part 5 (FIG. 4) and a second portion formed by the second housing part 15. In certain implementations, the first portion of the pump body interior 11 has substantially the same volume as the second portion of the pump body interior 11. In other implementations, however, the first portion may have a greater or lesser volume than the second portion. A piston 12 is configured to move (e.g., reciprocate) through the passage 11 along a vertical axis $A_R$ (FIG. 4) to increase or decrease the volume of the pump body interior 11.

In some implementations, a piston driver 13 is attached to one end of the piston 12. In other implementations, the piston driver 13 is integral with the piston 12. In certain implementations, the piston driver 13 is configured to slide along a track 16 provided at the upper housing part 15 (see FIG. 3). In the example shown, the track 16 is external of the upper housing part 15. The piston driver 13 is controlled by the control unit 224 (FIGS. 1A and 1B) to move the piston 12 axially within the pump body interior 11. For example, the control unit 224 may move the piston driver 13 upwardly and downwardly along the track 16.

The lower housing part 5 provides connector arrangement 10 by which the pump module 216 may connected to a lactate monitoring system (e.g., to a control unit 224 of FIG. 1A). In some implementations, the connector arrangement 10 defines one or more openings through which a fastener may pass to secure the pump module 216 to a surface. In other implementations, the connector arrangement 10 includes fingers, pegs, tabs, or other such members that are configured to interface with structure of the lactate monitoring system. The piston driver 13 also may include structure for interfacing with the lactate monitoring system.

Figure 5:
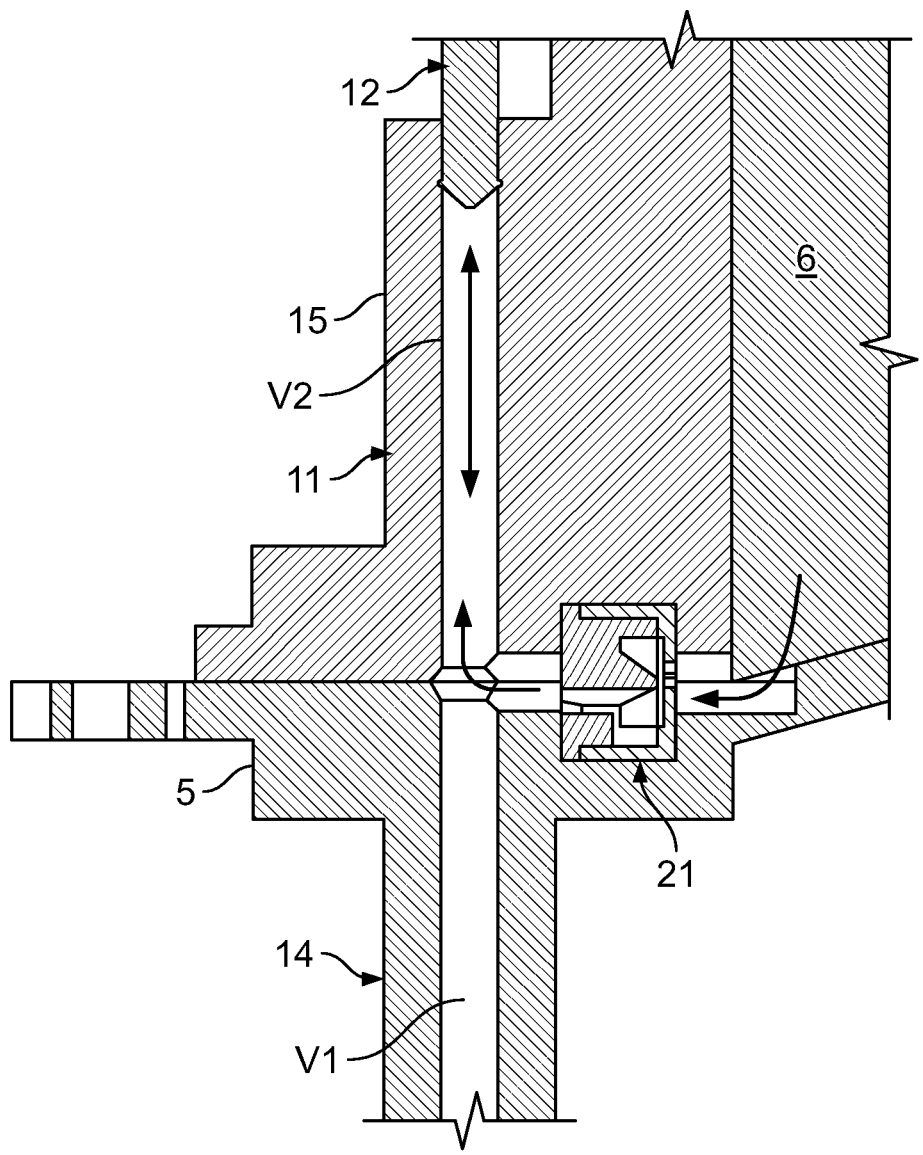
FIG. 5 is a flow routing diagram showing a calibration fluid flow path between a reservoir and a pump body during a second cycle of the pump module duty cycle.

The pump body has a first port 17 (FIG. 3) coaxial with the piston 12 at which the outlet fluid line 14 is connected to the pump body to create the second flow path 223, 223' of FIGS. 1A and 1B, respectively. The pump body also has a second port 18 (FIG. 6) defined at a circumferential wall of the pump body interior 11 at which the check valve 21 is connected to the pump body via a reservoir flow path 9. As noted above, the reservoir flow path 9 to the check valve 21 divides the pump body interior into a first volume V1 and a second volume V2 (see FIG. 5). In some implementations, the reservoir flow path 9 is located at an axial center of the pump body interior 11 (see FIG. 3). In other implementations, the reservoir flow path 9 is located offset from an axial center of the pump body interior 11.

Two components providing access to the reservoir 4 are located at the topmost portion of the second housing 15 on the pump module 216. A first of the components includes a fill septum 1 and a second of the components includes an air vent 3. The fill septum 1 provides a channel through which the reservoir 4 may be filled with the anticoagulant/calibrant fluid mixture during or subsequent to manufacture of the pump module 216. In one example implementation, the fill septum 1 is a silicone-rubber fill septum 1.

Figure 7:
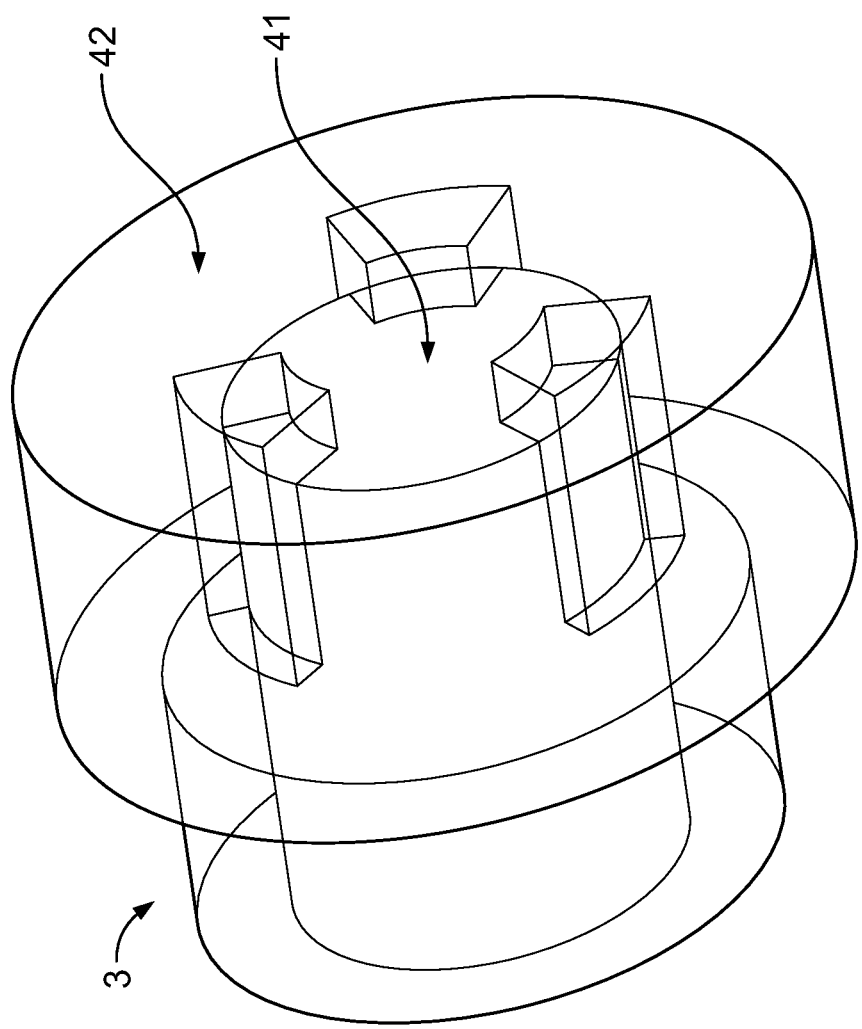
FIG. 7 is a schematic depiction of an embodiment of an air vent plug.

The air vent 3 provides a channel to allow air to be displaced from the reservoir 4 as the calibration fluid is either added (e.g., during manufacture) or depleted (e.g., during the normal operation of the pump module 216) without the need for complex valve mechanisms. In one example implementation, the air vent 3 is a non-woven Teflon® air vent 3. FIG. 7 illustrates one example implementation of an air vent 3 suitable for use with the pump module 216 of FIGS. 2-5. The air vent 3 includes a Gortex, non-woven, vent structure 41 and molded poly plug 42.

As discussed above, the duty cycle of the pump module 216 includes a wash cycle, during which calibration fluid is provided to the sensor, and a test cycle, during which a blood sample is provided to the sensor. Accordingly, the piston driver 13 moves the piston 12 in a reciprocating pattern to create bidirectional flow of fluid through an outlet fluid line 14 during operation. In some implementations, the duty cycle is implemented over a time period of about 8 hours. In other implementations, the duty cycle is implemented over a longer or shorter period of time. The duty cycle may be repeated periodically to monitor trends in the analyte (e.g., glucose, lactate, etc.) levels of the patient. In some implementations, the duty cycle of the pump module 216 also includes a refill cycle during which the pump module 216 obtains fresh calibration fluid from the reservoir 4. In other implementations, the pump module 216 obtains the calibration fluid during one of the wash cycle and the test cycle.

During the wash cycle, the piston 12 moves downwardly towards the first port 17, thereby pushing a volume of calibration fluid towards the patient to provide a calibration and anticoagulant wash to the outlet fluid line 14 and to the downstream sensor (e.g., sensor 214, 214' of FIGS. 1A, 1B, respectively). In particular, the piston 12 pushes any calibration fluid contained in the pump body towards the first outlet 17 and into the outlet flow line 14. The check valve 21 inhibits the calibration fluid from returning to the reservoir 4 through the reservoir flow path 9. Pushing the calibration fluid from the pump body into the outlet line 14 causes the calibration fluid that was contained in the outlet line 14 to move towards the sensor.

During the test cycle, the piston 12 moves upwardly away from the first port 17 along the first volume V1 of the pump body interior 11 to draw a patient blood sample and to "pull" the blood sample across the sensor where the blood analysis is taken. At the start of the second cycle, the piston 12 extends across the second port 18 and blocks access the reservoir flow line 9. Accordingly, movement of the piston 12 through the first volume V1 does not pull calibration fluid from the reservoir 4 into the pump body interior 11. As noted above, the first volume V1 of the pump body interior 11 is at least as large as a combined volume of the first flow line between the patient and the sensor, the test chamber within the sensor, and a diffusion barrier extending from the sensor along the outlet fluid line 14. Accordingly, movement of the piston 12 through the volume V1 is sufficient to pull a non-diffused blood sample through the first flow line and across the sensor.

During a refill cycle, the piston 12 passes the second port 18 as the piston 12 continues to move upwardly, thereby unblocking access to the reservoir flow line 9. When the second port 18 is unblocked by the piston 12, upward movement of the piston 12 through the second volume V2 of the pump body interior 11 pulls calibration fluid from the reservoir 4 through the check valve 21 and into the pump body interior 11 (e.g., see FIG. 5). As noted above, in some implementations, the diameter or transverse cross-sectional area of the reservoir flow path 9 is much larger than the diameter or transverse cross-sectional area of the outlet fluid line 14. Accordingly, the differential pressure gradient between the two ports 17, 18 caused by continued upward movement of the piston 12 results in fluid flow through only the second port 18. Therefore, upward movement of the piston 12 through the second volume V2 fills the second volume V2 with calibration fluid without further drawing blood from the patient.

Figure 6:
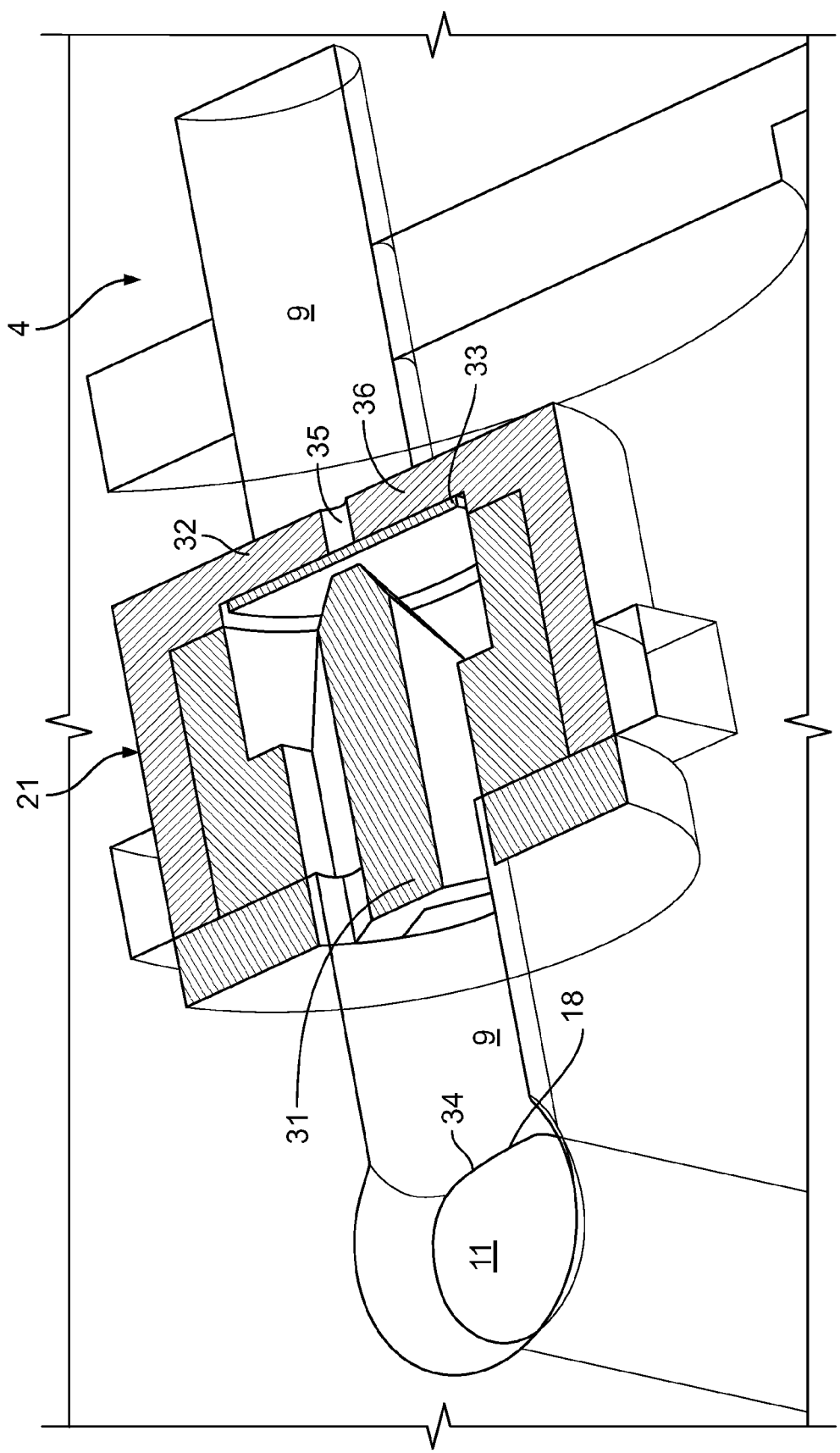
FIG. 6 is a schematic depiction of a sectional view of an example check valve of the pump module with the sectional view taken between an upper housing and a lower housings looking toward the upper cylinder passage of the pump body.

FIG. 6 illustrates one example implementation of a check valve sub-assembly 21 suitable for use with the pump module 216. The check valve 21 is located within the cylindrical passage 9 joining the pump cylinder 11 and the reservoir 4. The check valve 21 includes a valve body 31, a valve seat 32, and a valve diaphragm 33. A planar surface of the diaphragm 33 faces a wall or plate 36 defining one or more holes 35. In the example shown in FIG. 6, the plate 36 defines one hole 35. In other implementations, the plate 36 defines an array of holes 35. In certain implementations, the holes 35 defined in the plate 36 are about 0.015 inches is diameter. In other implementations, the holes 35 may be larger or smaller.

Fluid flow is directed from the reservoir 4, through the check valve 21, and toward the pump cylinder 11 during the second cycle after the piston 12 has passed the second port 18. In the example shown, fluid flow is directed toward the pump cylinder 11 when the piston 12 passes a chamfer 34 between the pump cylinder 11 and the reservoir flow path 9. When the piston 12 reverses direction and begins to move towards the first port 17, a diaphragm 33 is forced against a valve seat 32 covering the holes 35 in the plate 36. Covering the holes 35 prevents flow into the reservoir chamber 4 during the "push" cycle of the piston motion. When the piston 12 clears the second port 18 during the downward movement cycle, the check valve 21 again allows flow to enter the cylinder 11 and fill the space behind the piston 12 as the piston moves towards the first port 17.

Figure 8:
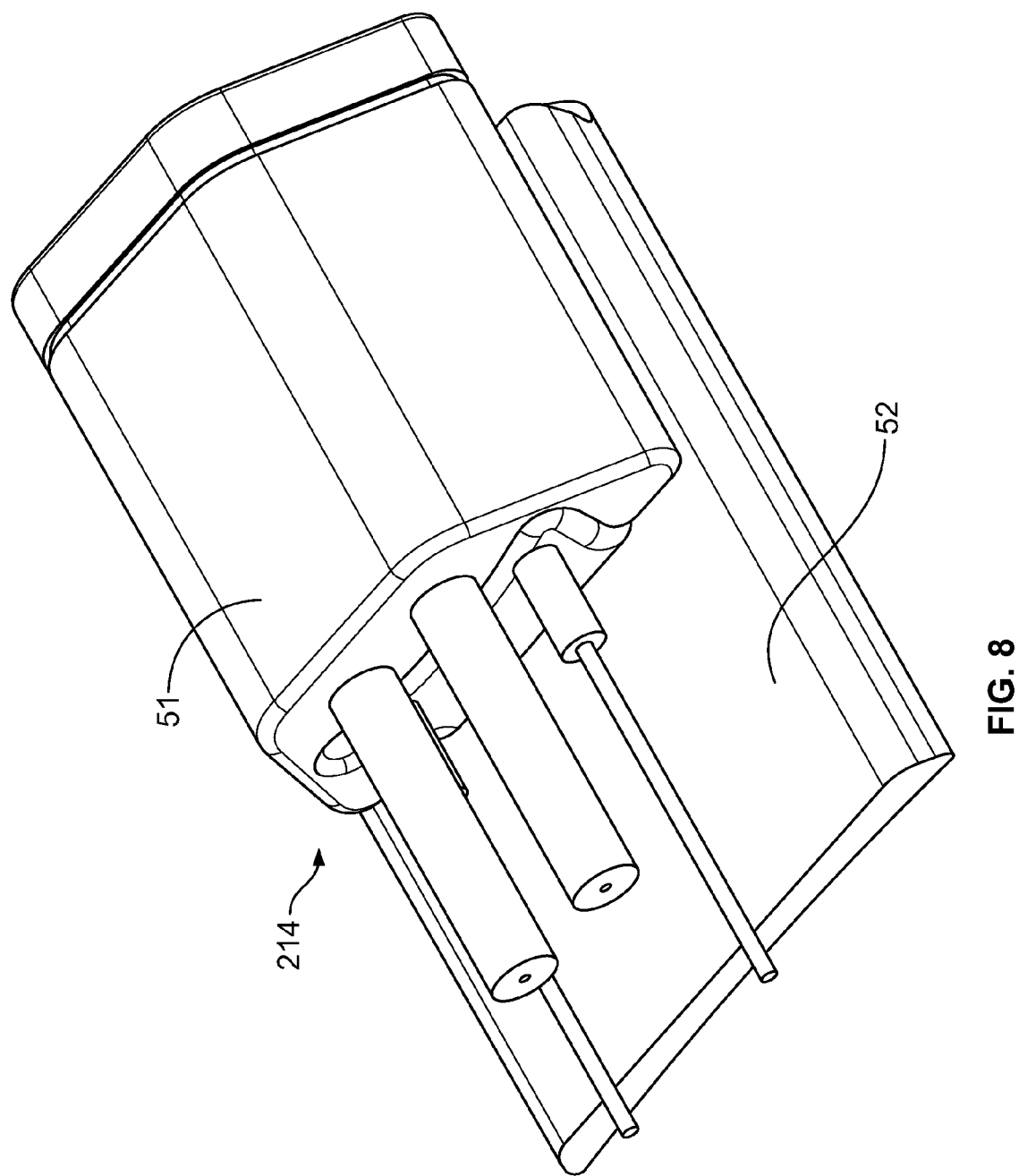
FIG. 8 is a schematic depiction of one example embodiment of an ex-vivo planar sensor suitable for use in the sensor system of FIG. 1A.
Figure 9:
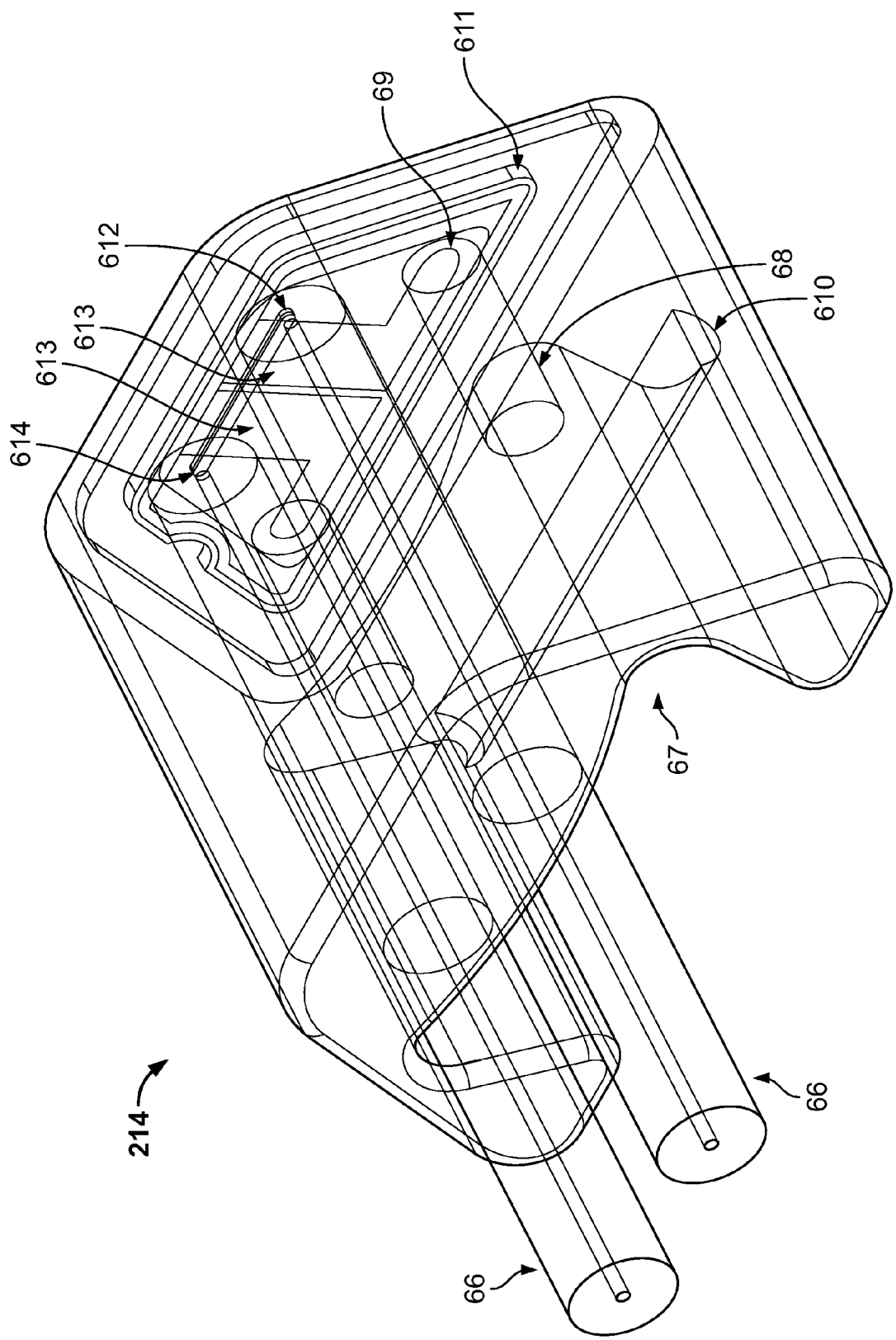
FIG. 9 is a schematic depiction of an embodiment of a fluid connector portion of the ex-vivo planar sensor of FIG. 8.
Figure 10:
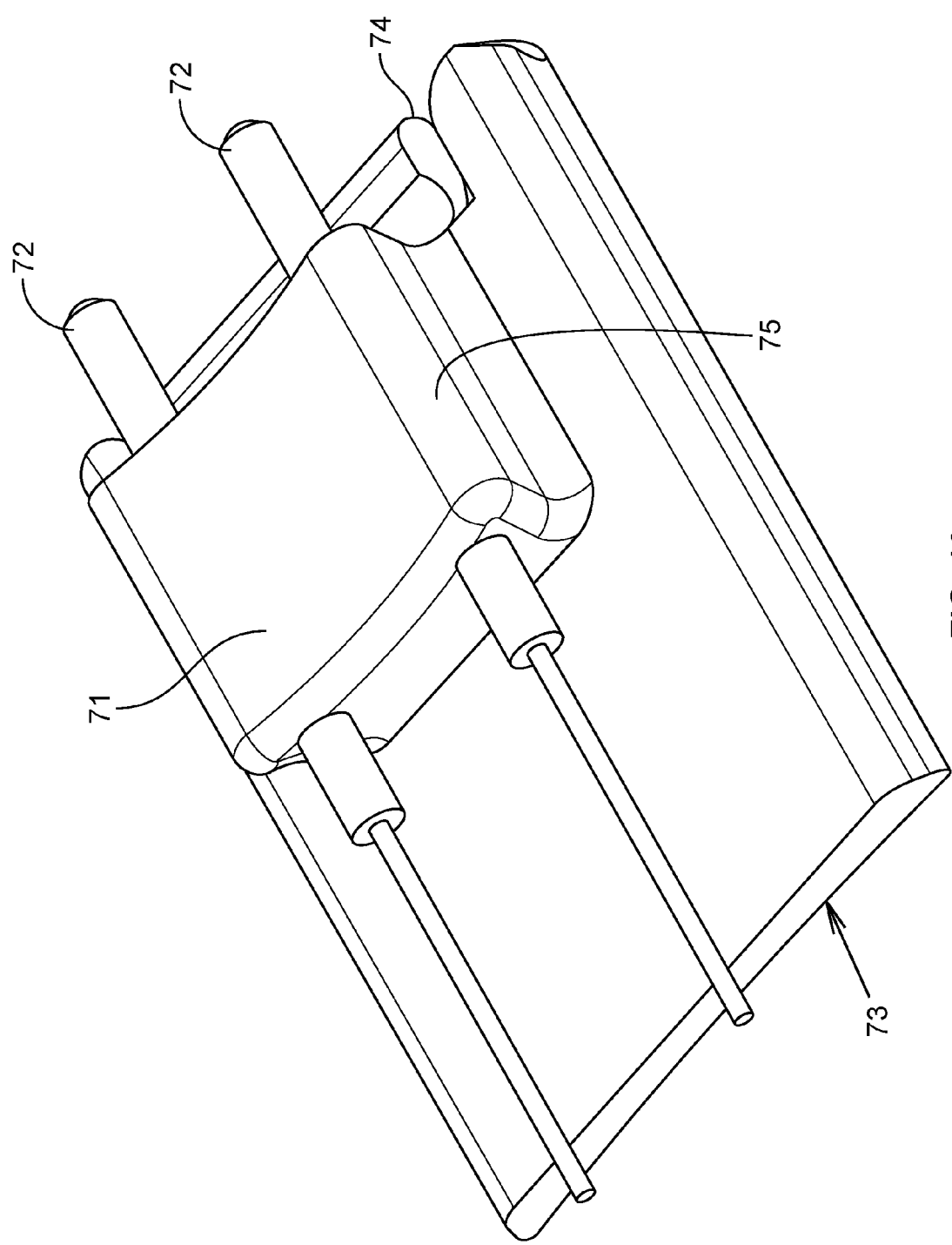
FIG. 10 is a schematic depiction of an embodiment of an electrical connector skin mount portion of the ex-vivo planar sensor of FIG. 8.

FIG. 8-10 illustrates one example implementation of an ex-vivo sensor 214 suitable for use with the pump module 216 of FIGS. 2-5 and with the sensor system 210 shown in FIG. 1. The sensor 214 includes a planar sensor 11 (FIG. 9), an electrical connector skin mount 52 (FIG. 10), and a fluid connector 51 (FIG. 8).

FIG. 9 illustrates a detailed view of the fluid connector 51 of FIG. 8. The sensor 611 includes at least two conductive traces serving as an electrode array 613. In some implementations, the sensor 611 is fabricated as a screen-printed array deposed on a polymer film. The electrode array is configured so as to be perpendicular to entry ports 612 that are configured to receive two tubular connectors of the fluid connector 51 of FIG. 8 when the sensor 611 is mated to the fluid connector 51. The printed electrode array 613 is patterned so as to provide two or more electrically isolated electrode pads on a facing plane common to the entry ports and aligned so that a fluid path channel 614 formed in the fluid connector portion of the sensor housing that links the two entry ports will completely traverse a portion of the electrode array in transit from one entry port to the other. The two entry port passages in turn provide connective means for two flexible tube components 66 of identical cross sectional dimensions.

A first of the flexible tube component 66 links the fluid connector portion of the sensor housing to a pump/reservoir assembly, such as reservoir 4 of FIGS. 2-3. A second of the flexible tube components 66 links the fluid connector portion of the sensor housing to a patient access port (e.g., of the catheter). In one implementation, the catheter is an I.V. Peripheral Infusion Catheter (PIC). The flexible tube component interface is provided at the anterior vertical face of the fluid connector in the form of two cavities that provide structure to receive the flexible tube components for bonding: to make the fluidics assembly, set the depth of insertion for the flexible tube components in relationship to the sensor interface, and provide positions for the entry port passages and the communicating channel between the two entry port passages 612. Along the same axis of the entry port passages a mating feature 67 is provided for the guide rail boss feature of the electrical connector skin mount.

FIG. 10 illustrates a detailed view of the electrical connector skin mount 52 of FIG. 8. The electrical connector skin mount (ECSM) 52 is configured to provide electrical communication between the sensor 611 and the monitoring system. The ECSM 52 is affixed to the patient (e.g., by adhesive tape or by an integrated adhesive film patterned on the mounting surface 73). Distal to that mounting surface the ECSM 52 is configured with a guide rail boss feature 71 that carries two conductive spring pins 72 parallel to the mounting surface plane. The spring pins protrude beyond the posterior vertical surface of the ECSM sufficiently so as to pass through two guiding cylindrical passages so aligned as to provide access of the conductive spring pins to the output contacts of the sensor electrode array contained within the fluid connector. The guide rail 75 functions to support the fluid connector mounting process by the user by providing the initial alignment necessary to position the spring pins and direct them to the mating position with the sensor. A third feature of the ECSM 52 is a retention snap-latch 74 located at the posterior portion of the ECSM 52. The retention snap-latch 74 mates to latch an opposing feature 67 provided on the fluid connector of the FIG. 9.

Additional details pertaining to example ex vivo sensors can be found in U.S. Pat. No. 6,117,290, the disclosure of which is incorporated by reference above. For example, FIGS. 11-17 and the accompanying text disclose one example implementation of an ex vivo sensor 214 suitable for use with the sensor system 210 of FIG. 1A.

Figure 11:
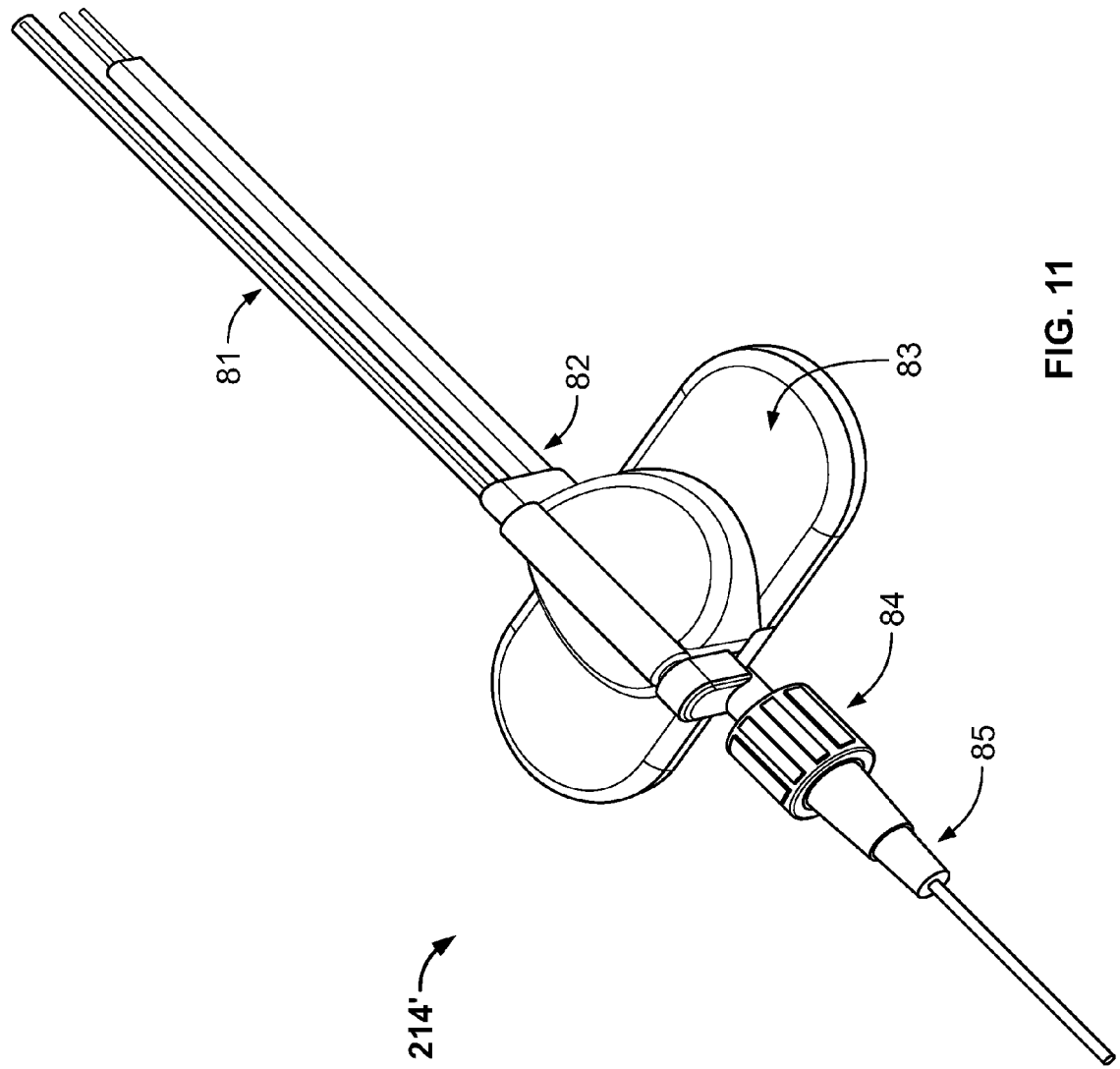
FIG. 11 is a schematic depiction of one example embodiment of an in-vivo planar sensor suitable for use in the sensor system of FIG. 1B.
Figure 12:
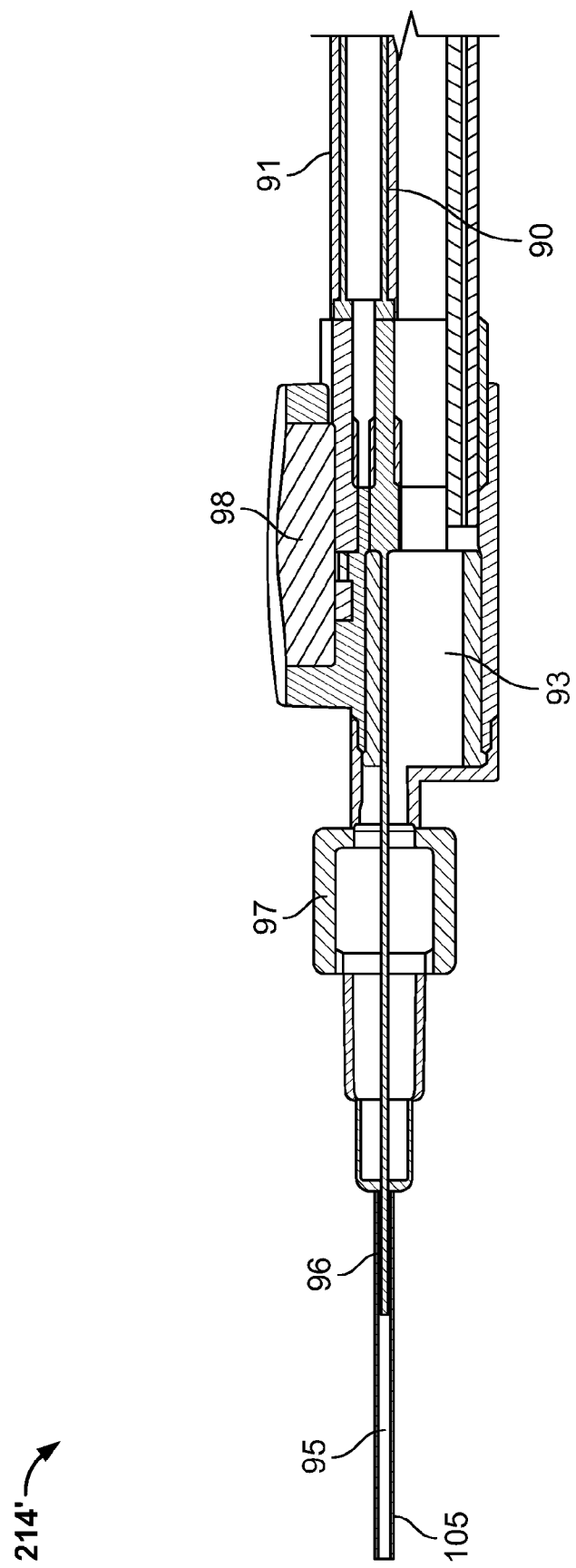
FIGS. 12 and 13 are schematic depictions of a longitudinal cross-section of the in-vivo sensor of FIG. 11.
Figure 13:
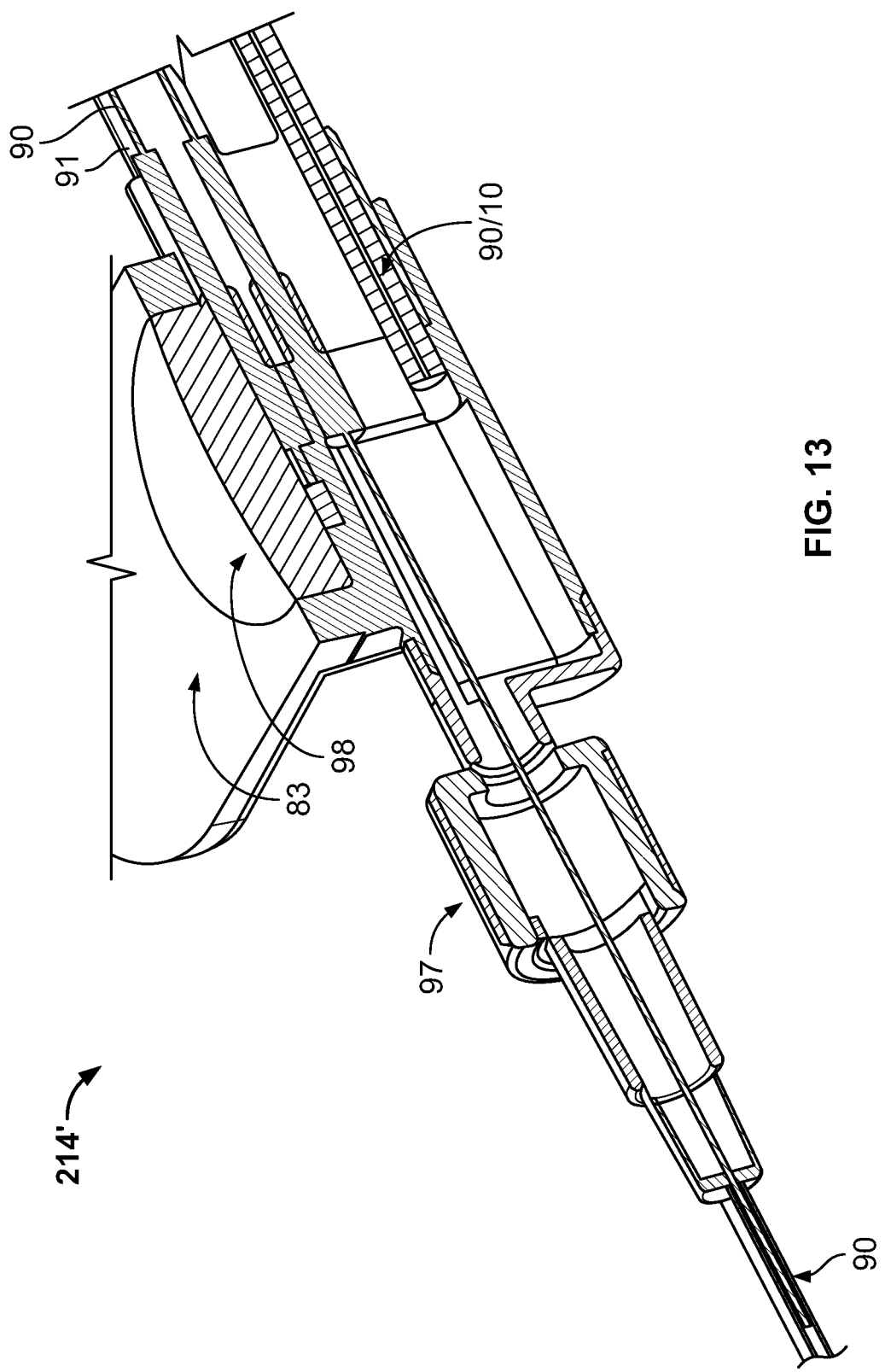

FIGS. 11-13 illustrate one example implementation of an in-vivo sensor 214' suitable for use with the pump module 216 of FIGS. 2-5 and the sensor system 210' of FIG. 1B. As shown in FIG. 11, the example in vivo sensor 214' includes a fluid connection 81 to a pump module 216, a CCM fiber and connector harness 82 connected to the monitoring system (e.g., control unit 224), skin mount 83 with gel electrode pad on a proximal surface thereof for positioning of the in-vivo sensor 214' at the patient's skin, a luer connection 84, and a PIC catheter 85.

FIG. 12 illustrates a longitudinal cross-section of the in-vivo sensor 214' of FIG. 11. This view shows a CCM working electrode 90, which resides within a catheter sheath 96. The terminus of the sensor 214' being sufficiently distal from the catheter sheath lumen 105 to limit the effects of diffusion between the blood sample and the calibration fluid. The fluid path through the indwelling catheter to the patient capillary access is routed through a molded component providing both an electrical connection and a fluid connection to the sensor system 210'. A fluid/electrical connector 93 resides at the distal port of the PIC Catheter 95 and is connected to the PIC Catheter by means of a standard Luer Lock component 97. When connected and mounted to the approved patient access site (e.g., on the forearm, the back of the hand, or wrist) the CCM working electrode 90 is directly wired to the patient blood with a circuit made through a skin mounted gel electrode 98 and back to a lactate monitor through the conductor of 91.

Additional details pertaining to example in vivo sensors can be found in U.S. Publication No. 2010/0252430, the disclosure of which is incorporated by reference above. For example, FIGS. 6A-6C, 7, and 8 and the accompanying text disclose one example implementation of an in vivo sensor 214' suitable for use with the sensor system 210' of FIG. 1B.

With regard to the foregoing description, it is to be understood that changes may be made in detail, especially in matters of construction materials employed and the shape, size and arrangement of the parts without departing from the scope of the present disclosure. It is intended that the specification and depicted aspects be considered exemplary only, with a true scope and spirit of the disclosure being indicated by the broad meaning of the following claims.

The invention claimed is:

1. A lactate monitoring system comprising:
a pump including a piston that can be linearly moved in first and second opposite directions within a cylinder, the cylinder including a first end and a second end, the cylinder also including an end port positioned at the first end of the cylinder and a side port positioned between the first and second ends of the cylinder, the side port having a larger transverse cross-sectional area than the end port;
a reservoir containing calibrant and anticoagulant, the reservoir being fluidly connected to the side port of the cylinder such that the calibrant and anticoagulant can be drawn into the cylinder through the side port when the piston is moved in the second direction while an end of the piston is positioned between the side port and the second end of the cylinder;
a fluid flow line that extends from the end port to a patient blood sampling end of the fluid flow line, wherein the calibrant and anticoagulant are pushed out of the cylinder and into the fluid flow line when the piston is moved in the first direction within the cylinder, and wherein a blood sample is drawn into the patient blood sampling end of the fluid flow line when the piston is moved in the second direction while the end of the piston is between the side port and the first end of the cylinder; and
a lactate sensor positioned along the fluid flow line.

2. The lactate monitoring system of claim 1, wherein the pump draws fluid from the flow line when the piston is moved in the second direction within the cylinder while an end of the piston is between the first end of the cylinder and the side port, and wherein the pump draws calibrant and anticoagulant from the reservoir when the piston is moved in the second direction within the cylinder when the end of the piston is between the side port and the second end of the cylinder.

3. The lactate monitoring system of claim 1, wherein the transverse cross-sectional area of the side port is at least 2 times as large as a transverse cross-sectional area of the end port.

4. The lactate monitoring system of claim 1, wherein the reservoir is formed by a housing that is integrally/unitarily molded with the cylinder.

5. The lactate monitoring system of claim 1, wherein the reservoir includes a vent.

6. The lactate monitoring system of claim 5, wherein the reservoir includes a fill port.

7. The lactate monitoring system of claim 1, wherein the flow line defines a blood intake volume that extends from the patient blood sampling end to the lactate sensor, wherein the cylinder defines a first volume between the first end of the cylinder and the side port, and wherein the first volume is at least as large as the blood intake volume plus a volume of a diffusion barrier between blood in the flow line and the calibrant and anticoagulant in the flow line.

* * * * *